US008197665B2

(12) United States Patent
Krafft et al.

(10) Patent No.: US 8,197,665 B2
(45) Date of Patent: Jun. 12, 2012

(54) AQUEOUS COMPOSITION CONTAINING A SALT, MANUFACTURING PROCESS AND USE

(75) Inventors: Philippe Krafft, Rhode Saint Genese (BE); Patrick Gilbeau, Braine-le-comte (BE); Dominique Balthasart, Brussels (BE); Andre Daene, Waterloo (BE)

(73) Assignee: Solvay (Societe Anonyme), Brussels (BE)

( * ) Notice: Subject to any disclaimer, the term of this patent is extended or adjusted under 35 U.S.C. 154(b) by 235 days.

(21) Appl. No.: 12/663,753

(22) PCT Filed: Jun. 11, 2008

(86) PCT No.: PCT/EP2008/057245
§ 371 (c)(1),
(2), (4) Date: Dec. 9, 2009

(87) PCT Pub. No.: WO2008/152043
PCT Pub. Date: Dec. 18, 2008

(65) Prior Publication Data
US 2010/0170805 A1 Jul. 8, 2010

(30) Foreign Application Priority Data
Jun. 12, 2007 (FR) .................................. 07 55697
Jan. 31, 2008 (EP) .................................. 08150927

(51) Int. Cl.
*C25C 1/02* (2006.01)
(52) U.S. Cl. ........ 205/620; 205/618; 205/334; 205/346; 205/498; 252/182.32; 210/748.13; 210/748.16; 210/749; 210/756
(58) Field of Classification Search ............. 252/182.32; 210/748.13, 748.16, 749, 756; 205/334, 205/346, 498, 618, 620
See application file for complete search history.

(56) References Cited

U.S. PATENT DOCUMENTS

| | | |
|---|---|---|
| 280,693 A | 7/1883 | Baijjard |
| 865,727 A | 9/1907 | Queneau |
| 2,060,715 A | 11/1936 | Arvin |
| 2,063,891 A | 12/1936 | Dreyfus |
| 2,144,612 A | 1/1939 | Britton et al. |
| 2,198,600 A | 4/1940 | Britton et al. |
| 2,248,635 A | 7/1941 | Marple et al. |
| 2,319,876 A | 5/1943 | Moss |
| 2,444,333 A | 6/1948 | Castan |
| 2,505,735 A | 4/1950 | Halbedel |
| 2,726,072 A | 12/1955 | Herman |
| 2,811,227 A | 10/1957 | O'Connor |
| 2,829,124 A | 4/1958 | Napravnik et al. |
| 2,860,146 A | 11/1958 | Furman et al. |
| 2,876,217 A | 3/1959 | Paschall |
| 2,945,004 A | 7/1960 | Greenlee |
| 2,960,447 A | 11/1960 | Anderson et al. |
| 3,026,270 A | 3/1962 | Robinson, Jr. |
| 3,052,612 A | 9/1962 | Henegar et al. |
| 3,061,615 A | 10/1962 | Viriot et al. |
| 3,121,727 A | 2/1964 | Baliker et al. |
| 3,135,705 A | 6/1964 | Vandenberg |
| 3,158,580 A | 11/1964 | Vandenberg |
| 3,158,581 A | 11/1964 | Vandenberg |
| 3,247,227 A | 4/1966 | White |
| 3,260,059 A | 7/1966 | Rosenberg et al. |
| 3,341,491 A | 9/1967 | Robinson et al. |
| 3,355,511 A | 11/1967 | Schwarzer |
| 3,385,908 A | 5/1968 | Schwarzer |
| 3,445,197 A | 5/1969 | Resh et al. |
| 3,457,282 A | 7/1969 | Polak et al. |
| 3,618,295 A | 11/1971 | Geiger et al. |
| 3,711,388 A | 1/1973 | Gritzner |
| 3,766,221 A | 10/1973 | Becker |
| 3,839,169 A | 10/1974 | Moyer |
| 3,865,886 A | 2/1975 | Schindler et al. |
| 3,867,166 A | 2/1975 | Sullivan |
| 3,954,581 A | 5/1976 | Carlin |
| 3,968,178 A | 7/1976 | Obrecht et al. |
| 4,003,723 A | 1/1977 | Schafer et al. |
| 4,011,251 A | 3/1977 | Tjurin et al. |
| 4,024,301 A | 5/1977 | Witenhafer et al. |
| 4,127,594 A | 11/1978 | Anderson et al. |
| 4,173,710 A | 11/1979 | Boulet et al. |
| 4,197,399 A | 4/1980 | Noel et al. |
| 4,220,529 A | 9/1980 | Daude-Lagrave |
| 4,240,885 A | 12/1980 | Suciu et al. |

(Continued)

FOREIGN PATENT DOCUMENTS

| | | |
|---|---|---|
| CN | 1296003 A | 5/2001 |
| CN | 101041421 | 9/2007 |

(Continued)

OTHER PUBLICATIONS

Medium and Long-term Opportunities and Risks of the Biotechnological Production of Bulk Chemicals from renewable Resources—The Potential of White Technology—The BREW project—Final Report—prepared under the European Commission GRXTH Programme (DG Research) Ulrecht, Sep. 2006 (pp. 29-31).
Ullmann's Encyclopedia Industrial Chemistry, $5^{th}$ Ed. vol. A6 (1988) pp. 401-477.
Polymer Science Dictionary, M.S.M., Elsevier Applied Chemistry, London & New York, 1989 p. 86.
Perry's Chemical Engineers' Handbook, $6^{th}$ Edition, Section 21, pp. 21-55.
E. Milchert et al., "Installation for the Recovery of Dichloropropanols and Epichlorohydrin from the Waste Water in Epichlorohydrin Production", Pol. J. Appl. Chem., vol. 41, p. 113-118 (1997).

(Continued)

*Primary Examiner* — Bruce Bell
(74) *Attorney, Agent, or Firm* — Oblon, Spivak, McClelland, Maier & Neustadt, L.L.P.

(57) ABSTRACT

Aqueous composition containing at least one salt in an amount of at least 30 g/kg of composition, of which the total organic carbon content is at least 1 µg of C/l and at most 5 g of C/l of composition and which contains at least one carboxylic acid.

19 Claims, 4 Drawing Sheets

U.S. PATENT DOCUMENTS

| | | | |
|---|---|---|---|
| 4,255,470 A | 3/1981 | Cohen et al. | |
| 4,294,776 A | 10/1981 | Hardy et al. | |
| 4,390,680 A | 6/1983 | Nelson | |
| 4,405,465 A | 9/1983 | Moore et al. | |
| 4,415,460 A | 11/1983 | Suciu et al. | |
| 4,464,517 A | 8/1984 | Makino et al. | |
| 4,499,255 A | 2/1985 | Wang et al. | |
| 4,595,469 A | 6/1986 | Foller | |
| 4,609,751 A | 9/1986 | Hajjar | |
| 4,634,784 A | 1/1987 | Nagato et al. | |
| 4,655,879 A | 4/1987 | Brockmann et al. | |
| 4,935,220 A | 6/1990 | Schneider et al. | |
| 4,960,953 A | 10/1990 | Jakobson et al. | |
| 4,973,763 A | 11/1990 | Jakobson et al. | |
| 4,990,695 A | 2/1991 | Buenemann et al. | |
| 5,041,688 A | 8/1991 | Jakobson et al. | |
| 5,200,163 A | 4/1993 | Henkelmann et al. | |
| 5,227,030 A * | 7/1993 | Beaver et al. | 205/532 |
| 5,278,260 A | 1/1994 | Schaffner et al. | |
| 5,286,354 A | 2/1994 | Bard et al. | |
| 5,344,945 A | 9/1994 | Grunchard | |
| 5,359,094 A | 10/1994 | Teles et al. | |
| 5,393,428 A | 2/1995 | Dilla et al. | |
| 5,445,741 A | 8/1995 | Dilla et al. | |
| 5,478,472 A | 12/1995 | Dilla et al. | |
| 5,486,627 A | 1/1996 | Quarderer et al. | |
| 5,567,359 A | 10/1996 | Cassidy et al. | |
| 5,578,740 A | 11/1996 | Au et al. | |
| 5,679,839 A | 10/1997 | Armand et al. | |
| 5,710,350 A | 1/1998 | Jeromin et al. | |
| 5,731,476 A | 3/1998 | Shawl et al. | |
| 5,744,655 A | 4/1998 | Thomas et al. | |
| 5,779,915 A | 7/1998 | Becker et al. | |
| 5,908,946 A | 6/1999 | Stern et al. | |
| 5,993,974 A | 11/1999 | Fukushima et al. | |
| 6,024,829 A | 2/2000 | Schufeldt | |
| 6,103,092 A | 8/2000 | Silva | |
| 6,111,153 A | 8/2000 | Crow et al. | |
| 6,142,458 A | 11/2000 | Howk | |
| 6,177,599 B1 | 1/2001 | Cowfer et al. | |
| 6,270,682 B1 | 8/2001 | Santen et al. | |
| 6,288,248 B1 | 9/2001 | Strebelle et al. | |
| 6,288,287 B2 | 9/2001 | Ueoka et al. | |
| 6,350,888 B1 | 2/2002 | Strebelle et al. | |
| 6,350,922 B1 | 2/2002 | Vosejpka et al. | |
| 6,521,794 B2 | 2/2003 | Hirota | |
| 6,719,957 B2 | 4/2004 | Brady, Jr. et al. | |
| 6,740,633 B2 | 5/2004 | Norenberg et al. | |
| 6,831,201 B2 | 12/2004 | Katsuura et al. | |
| 7,126,032 B1 | 10/2006 | Aiken | |
| 7,128,890 B2 | 10/2006 | Ollivier | |
| 7,557,253 B2 | 7/2009 | Gilbeau | |
| 7,584,629 B2 | 9/2009 | Sohn et al. | |
| 7,615,670 B2 | 11/2009 | Gilbeau | |
| 2001/0014763 A1 | 8/2001 | Ueoka et al. | |
| 2003/0209490 A1 | 11/2003 | Camp et al. | |
| 2004/0016411 A1 | 1/2004 | Joyce et al. | |
| 2004/0024244 A1 | 2/2004 | Walsdorff et al. | |
| 2004/0047781 A1 | 3/2004 | Becenel | |
| 2004/0150123 A1 | 8/2004 | Strofer et al. | |
| 2004/0179987 A1 | 9/2004 | Oku et al. | |
| 2004/0232007 A1 | 11/2004 | Carson et al. | |
| 2005/0115901 A1 | 6/2005 | Heuser et al. | |
| 2005/0261509 A1 | 11/2005 | Delfort et al. | |
| 2006/0052272 A1 | 3/2006 | Meli et al. | |
| 2006/0079433 A1 | 4/2006 | Hecht et al. | |
| 2006/0123842 A1 | 6/2006 | Sohn et al. | |
| 2007/0112224 A1 | 5/2007 | Krafft et al. | |
| 2007/0293707 A1 | 12/2007 | Wolfert et al. | |
| 2008/0053836 A1 | 3/2008 | Bulan et al. | |
| 2008/0146753 A1 | 6/2008 | Woike et al. | |
| 2008/0154050 A1 | 6/2008 | Gilbeau | |
| 2008/0161613 A1 | 7/2008 | Krafft et al. | |
| 2008/0194847 A1 | 8/2008 | Krafft et al. | |
| 2008/0194849 A1 | 8/2008 | Krafft et al. | |
| 2008/0194851 A1 | 8/2008 | Gilbeau | |
| 2008/0200642 A1 | 8/2008 | Krafft | |
| 2008/0200701 A1 | 8/2008 | Krafft et al. | |
| 2008/0207930 A1 | 8/2008 | Gilbeau et al. | |
| 2008/0214848 A1 | 9/2008 | Krafft et al. | |
| 2008/0281132 A1 | 11/2008 | Krafft et al. | |
| 2009/0022653 A1 | 1/2009 | Strebelle et al. | |
| 2009/0131631 A1 | 5/2009 | Krafft et al. | |
| 2009/0173636 A1 | 7/2009 | Ooms et al. | |
| 2009/0198041 A1 | 8/2009 | Krafft et al. | |
| 2009/0270588 A1 | 10/2009 | Krafft et al. | |
| 2009/0275726 A1 | 11/2009 | Krafft et al. | |
| 2010/0029959 A1 | 2/2010 | Fan et al. | |
| 2010/0032617 A1* | 2/2010 | Gilbeau et al. | 252/182.12 |
| 2010/0105862 A1 | 4/2010 | Krafft et al. | |
| 2010/0105964 A1 | 4/2010 | Krafft et al. | |
| 2010/0193732 A1* | 8/2010 | Hook et al. | 252/182.32 |
| 2010/0294727 A1* | 11/2010 | Gilbeau et al. | 210/748.13 |
| 2011/0028683 A1 | 2/2011 | Gilbeau et al. | |
| 2011/0152545 A1 | 6/2011 | Balthasart et al. | |
| 2011/0166369 A1 | 7/2011 | Krafft et al. | |
| 2011/0237773 A1 | 9/2011 | Gilbeau | |

FOREIGN PATENT DOCUMENTS

| | | |
|---|---|---|
| DE | 58396 C | 8/1891 |
| DE | 180668 C | 1/1906 |
| DE | 197308 C | 11/1906 |
| DE | 238341 C | 3/1908 |
| DE | 197309 C | 4/1908 |
| DE | 869 193 | 3/1953 |
| DE | 1041488 B | 10/1958 |
| DE | 1075103 B | 2/1960 |
| DE | 1226554 B | 10/1966 |
| DE | 2 241 393 | 2/1974 |
| DE | 25 21 813 | 12/1975 |
| DE | 3003819 A1 | 8/1981 |
| DE | 3243617 | 5/1984 |
| DE | 216471 A1 | 12/1984 |
| DE | 3721003 C1 | 12/1988 |
| DE | 43 02 306 | 8/1994 |
| DE | 43335311 A1 | 4/1995 |
| DE | 10203914 C1 | 10/2003 |
| DE | 10254709 A1 | 6/2004 |
| EP | 0 296 341 | 12/1988 |
| EP | 0347618 A2 | 12/1989 |
| EP | 0358255 A1 | 3/1990 |
| EP | 0421379 A1 | 4/1991 |
| EP | 0 452 265 | 10/1991 |
| EP | 0518765 A1 | 12/1992 |
| EP | 0522382 A1 | 1/1993 |
| EP | 0535949 B1 | 4/1993 |
| EP | 0561441 A1 | 9/1993 |
| EP | 0563720 A1 | 10/1993 |
| EP | 0568389 A1 | 11/1993 |
| EP | 0582201 A2 | 2/1994 |
| EP | 0 618 170 | 10/1994 |
| EP | 0 916 624 | 5/1999 |
| EP | 0919551 A1 | 6/1999 |
| EP | 0 774 0450 | 2/2000 |
| EP | 1059278 A2 | 12/2000 |
| EP | 1106237 A1 | 6/2001 |
| EP | 1153887 A2 | 11/2001 |
| EP | 1163946 A1 | 12/2001 |
| EP | 1231189 A1 | 8/2002 |
| EP | 1298154 A1 | 4/2003 |
| EP | 1411027 A1 | 4/2004 |
| EP | 1752435 A1 | 2/2007 |
| EP | 1752436 A1 | 2/2007 |
| EP | 1760060 A1 | 3/2007 |
| EP | 1762556 A1 | 3/2007 |
| EP | 1770081 A1 | 4/2007 |
| EP | 1772446 A1 | 4/2007 |
| EP | 1775278 A1 | 4/2007 |
| EP | 2085364 | 8/2009 |
| FR | 1 306 231 | 10/1961 |
| FR | 1 417 388 | 10/1964 |
| FR | 1476073 A | 4/1967 |
| FR | 1 577 792 | 8/1968 |
| FR | 2151107 | 4/1973 |
| FR | 2180138 | 5/1973 |
| FR | 2 217 372 | 2/1974 |
| FR | 2565229 A1 | 12/1985 |

| | | |
|---|---|---|
| FR | 2752242 A1 | 2/1998 |
| FR | 2862644 A1 | 5/2005 |
| FR | 2868419 A1 | 10/2005 |
| FR | 2869612 A1 | 11/2005 |
| FR | 2869613 A1 | 11/2005 |
| FR | 2872504 A1 | 1/2006 |
| FR | 2881732 A1 | 8/2006 |
| FR | 2885903 A1 | 11/2006 |
| FR | 2 917 411 | 12/2006 |
| FR | 2 912 743 | 8/2008 |
| FR | 2913683 | 9/2008 |
| FR | 2913683 A1 | 9/2008 |
| FR | 2918058 A1 | 1/2009 |
| FR | 2925045 A1 | 6/2009 |
| FR | 2929611 A1 | 10/2009 |
| FR | 2935699 A1 | 3/2010 |
| FR | 2935968 A1 | 3/2010 |
| GB | 14767 A | 0/1914 |
| GB | 406345 | 8/1932 |
| GB | 404938 A | 1/1934 |
| GB | 467481 A | 6/1937 |
| GB | 541357 A | 11/1941 |
| GB | 679536 A | 9/1952 |
| GB | 702143 A | 1/1954 |
| GB | 736641 A | 9/1955 |
| GB | 799567 A | 8/1958 |
| GB | 984446 A | 2/1965 |
| GB | 984633 A | 3/1965 |
| GB | 1083594 A | 9/1967 |
| GB | 1286893 A | 8/1972 |
| GB | 1387668 A | 3/1975 |
| GB | 1 493 538 | 4/1975 |
| GB | 1414976 A | 11/1975 |
| GB | 2173496 A | 10/1986 |
| GB | 2336584 A | 10/1999 |
| HU | 2002-003023 | 3/2004 |
| JP | 3927230 B2 | 11/1939 |
| JP | 50-062909 | 5/1975 |
| JP | 51021635 B | 7/1976 |
| JP | 55041858 A | 3/1980 |
| JP | 5629572 | 3/1981 |
| JP | 5699432 | 8/1981 |
| JP | 61 112066 A | 5/1986 |
| JP | 62242638 A | 10/1987 |
| JP | 63195288 A | 8/1988 |
| JP | 2-137704 | 5/1990 |
| JP | 03014527 A | 1/1991 |
| JP | 03223267 A | 10/1991 |
| JP | 3223267 A | 10/1991 |
| JP | 04089440 A | 3/1992 |
| JP | 04-217637 | 8/1992 |
| JP | 625196 B2 | 4/1994 |
| JP | 06184024 A | 7/1994 |
| JP | 6321852 A | 11/1994 |
| JP | 859593 | 3/1996 |
| JP | 09-2999953 | 11/1997 |
| JP | 10139700 A | 5/1998 |
| JP | 1998218810 A | 8/1998 |
| JP | 20000344692 A | 12/2000 |
| JP | 2001-037469 | 2/2001 |
| JP | 2001-213827 A | 8/2001 |
| JP | 2001-261308 | 9/2001 |
| JP | 2001-1261581 A | 9/2001 |
| JP | 2002-02033 A2 | 1/2002 |
| JP | 20020038195 A | 2/2002 |
| JP | 20020265986 A | 9/2002 |
| JP | 2002-363153 A | 12/2002 |
| JP | 2003-89680 A | 3/2003 |
| JP | 2003081891 A | 3/2003 |
| JP | 2005007841 A2 | 1/2005 |
| JP | 2005097177 A2 | 4/2005 |
| JP | 2007-008698 | 1/2007 |
| JP | 2009-263338 | 11/2009 |
| KR | 900006513 | 11/1987 |
| KR | 1019920003099 B1 | 4/1992 |
| KR | 10-514819 B1 | 9/2005 |
| PL | 136598 | 3/1986 |
| PL | 162910 | 1/1994 |
| RD | 436093 | 8/2000 |
| SU | 123153 | 1/1959 |
| SU | 1125226 | 11/1984 |
| SU | 1159716 | 6/1985 |
| SU | 1685969 | 10/1991 |
| WO | WO 95/14639 | 6/1995 |
| WO | WO 96/15980 | 5/1996 |
| WO | WO 97/48667 | 12/1997 |
| WO | WO 96/07617 | 3/1998 |
| WO | WO 98/37024 | 8/1998 |
| WO | WO 99/14208 | 3/1999 |
| WO | WO 9932397 A1 | 7/1999 |
| WO | WO 0024674 A1 | 5/2000 |
| WO | WO 0141919 A1 | 6/2001 |
| WO | WO 0186220 A2 | 11/2001 |
| WO | WO 02/26672 A2 | 4/2002 |
| WO | WO 03/064357 | 8/2003 |
| WO | WO 2004/056758 | 7/2004 |
| WO | WO 2005021476 A1 | 3/2005 |
| WO | WO 2005054167 A1 | 6/2005 |
| WO | WO 2005/097722 | 10/2005 |
| WO | WO 2005/115954 | 12/2005 |
| WO | WO 2005/116004 | 12/2005 |
| WO | WO 2006020234 A1 | 2/2006 |
| WO | WO 2006/100311 A2 | 9/2006 |
| WO | WO 2006/100312 A2 | 9/2006 |
| WO | WO 2006/100313 A2 | 9/2006 |
| WO | WO 2006/100314 A1 | 9/2006 |
| WO | WO 2006/100315 A2 | 9/2006 |
| WO | WO 2006/100316 A1 | 9/2006 |
| WO | WO 2006/100317 A | 9/2006 |
| WO | WO 2006/100318 A2 | 9/2006 |
| WO | WO 2006/100319 A1 | 9/2006 |
| WO | WO 2006/100320 A2 | 9/2006 |
| WO | WO 2006/106153 A2 | 10/2006 |
| WO | WO 2006/106154 A1 | 10/2006 |
| WO | WO 2006/106155 A2 | 10/2006 |
| WO | WO 2007/054505 A2 | 5/2007 |
| WO | WO2007/144335 | 12/2007 |
| WO | WO 2008/101866 | 8/2008 |
| WO | WO2008/107468 | 9/2008 |
| WO | WO 2008/110588 | 9/2008 |
| WO | WO2008/145729 | 12/2008 |
| WO | WO 2008/147473 | 12/2008 |
| WO | WO 2008/152044 | 12/2008 |
| WO | WO 2008/152045 | 12/2008 |
| WO | WO 2009/000773 | 12/2008 |
| WO | WO 2009/016149 A2 | 2/2009 |
| WO | WO 2009026212 A1 | 2/2009 |
| WO | WO2009/043796 A1 | 4/2009 |
| WO | WO 2009/077528 | 6/2009 |
| WO | WO 2009/077528 A1 | 6/2009 |
| WO | WO 2009/095429 A1 | 8/2009 |
| WO | WO 2009/121853 | 10/2009 |
| WO | WO2009/121853 A1 | 10/2009 |
| WO | WO 2010/029039 A1 | 3/2010 |
| WO | WO 2010/029153 | 3/2010 |
| WO | WO 2010/029153 A1 | 3/2010 |
| WO | WO 2010/029639 | 3/2010 |
| WO | WO 2010/066660 | 6/2010 |

OTHER PUBLICATIONS

Kleiboehmer W., et al, Solvay Werk Rheinberg: Integrierte Prozesse Separierte Abwasserbehandlungen—Gewaesserschutz, Wasser, Abwasser 200 (Wissenschaftlich-technische Mitteilungen des Instituts Zur Foerderung der Wasserguerte- und Wassermengenwirtschaft e; V;—2005 p. 81/-8/5., vol. 5.

Klaus Weissermel, et al., "Industrial Organic Chemistry," ($3^{rd}$ Completely Revised Edition); VCH 1997. p. 93-98.

Klaus Weissermel, et al., "Industrial Organic Chemistry," ($3^{rd}$ Completely Revised Edition); VCH 1997. p. 276-277.

Klaus Weissermel, et al., "Industrial Organic Chemistry," ($3^{rd}$ Completely Revised Edition); VCH 1997. p. 347-355.

Ying Ling Liu, "Epoxy Resins from Novel Monomers with a Bis-(9,10-dihydro-9-oxa-10-oxide-10-phosphaphenanthrene-10-yl-) Substituent," Journal of Polymer Science: Part A: Polymer Chemistry, vol. 40, 359-368 (2002).

Ying Ling Liu, "Phosphorous-Containing Epoxy Resins from a Novel Synthesis Route," Journal of Applied Polymer Science, vol. 83, 1697-1701 (2002).
M. Schellentrager, "Untersuchungen zur oxidation Entfarbung aus gewahlter Reaktivfarbstoffe: Analyse der Abbauprodukte misteels hochauflosender LC-MS", Dissertation, XP 0002548413 (Jan. 1, 2006) w/ English Abstract.
U.S. Appl. No. 60/734,659, filed Nov. 8, 2005.
U.S. Appl. No. 60/734,627, filed Nov. 8, 2005.
U.S. Appl. No. 60/734,657, filed Nov. 8, 2005.
U.S. Appl. No. 60/734,658, filed Nov. 8, 2005.
U.S. Appl. No. 60/734,635, filed Nov. 8, 2005.
U.S. Appl. No. 60/734,634, filed Nov. 8, 2005.
U.S. Appl. No. 60/734,637, filed Nov. 8, 2005.
U.S. Appl. No. 11/915,046, filed Nov. 20, 2007, Krafft, et al.
U.S. Appl. No. 60/734,636, filed Nov. 8, 2005.
U.S. Appl. No. 11/915,088, filed Nov. 20, 2007, Krafft, et al.
U.S. Appl. No. 60/560,676, filed Apr. 8, 2004, Gilbeau, et al.
U.S. Appl. No. 61/013,680, filed Dec. 14, 2007, Krafft, et al.
U.S. Appl. No. 61/013,704, filed Nov. 14, 2007, Gilbeau, et al.
U.S. Appl. No. 61/013,676, filed Dec. 14, 2007, Borremans.
U.S. Appl. No. 61/013,707, filed Dec. 14, 2007, Krafft, et al.
U.S. Appl. No. 61/013,672, filed Dec. 14, 2007, Krafft, et al.
U.S. Appl. No. 61/013,713, filed Dec. 14, 2007, Gilbeau.
U.S. Appl. No. 61/013,710, filed Dec. 14, 2007, Krafft, et al.
U.S. Appl. No. 61/007,661, filed Dec. 14, 2007, Boulos, et al.
U.S. Appl. No. 12/600,018, filed Nov. 13, 2009, Borremans.
U.S. Appl. No. 12/663,749, filed Dec. 9, 2009, Krafft, et al.
U.S. Appl. No. 12/663,887, filed Dec. 10, 2009, Krafft, et al.
U.S. Appl. No. 12/663,744, filed Dec. 9, 2009, Boulos, et al.
Herman A. Bruson, et al., "Thermal Decomposition of Glyceryl Carbonates," Journal of the American Chemical Society, vol. 74, Apr. 1952 pp. 2100-2101.
Perry's Chemical Engineers Handbook 7th Ed., 11th Section, 1997, pp. 11.1-11.118 (submitted into two parts).
Perry's Chemical Engineers Handbook 7th Ed., 13th Section, 1997, pp. 13.1-13.108.
Perry's Chemical Engineers Handbook 7th Ed., 15th Section, 1997, pp. 15.1-15.47.
Ullmann's Encyclopedia of Industrial Chemistry 5th Ed., vol. A23, 1993, pp. 635-636.
Ullmann's Encyclopedia of Industrial Chemistry 5th Ed., vol. A13, 1989, p. 289.
Ullmann's Encyclopedia of Industrial Chemistry 5th Ed., vol. A11, 1988, pp. 354-360.
Attached certified Application No. FR 06.05325 filed Jun. 14, 2006 by Solvay S.A.—priority document to EP2007/55742 published as WO 2007/144335 (attached herein) 17 pgs.
Attached certified Application No. FR 07.53863 filed Mar. 15, 2007 by Solvay S.A. and published as FR2913683, 19 pgs (attached herein)—priority document to EP2007/55742 published as WO2007/144335 29 pgs (attached herein).
Gibson, "The preparation, properties, and uses of glycerol derivatives, Part III. The Chlorohydrins", 1931, Chemistry and Industry, Chemical Society, pp. 949-975.
Carre et al, 1931, "La transformation des alcools polyatomiques en mono-et en polychlorohydrines au moyen du chlorure de thionyle", Bulletin De La Societe Chimique De France, Societe Francaise De Chimie. Paris—ISSN 0037-8968, vol. 49, No. 49, pp. 1150-1154.
Fauconner, 1888, "Preparation de l'epichlorhydrine", Bull. Soc. Chim. FR, No. 50, pp. 212-214 (with enclosed translation in English).
Ullmann's Encyclopedia of Industrial Chemistry, "Industrially important epoxides", 1987, Fifth Completely Revised Edition, vol. A9, pp. 539-540.
Bonner et al, "The composition of constant boiling hydrochloric acid at pressures of 50 to 1220 millimeters", 1930, Journal of American Chemical Society, vol. 52, pp. 633-635.
Muskof et al, "Epoxy Resins" in Ullmann's Encyclopedia of Industrial Chemistry, 1987, 5th Ed., vol. A9, pp. 547-563.
Novelli, A., "The preparation of mono-and dichlorohydrins of glycerol", 1930, Anales Farmacia Bioquimica, vol. 1, pp. 8-19 (with English abstract).
Derwent Publications, AN 109:6092 CA, JP 62-242638, Oct. 23, 1987, 1 pg.
Derwent Publications, AN 1987-338139 [48], JP 62-242638, Oct. 23, 1987, 1 pg.
I. Miyakawa et al, Nagoya Sangyo Kagaku Kenkyusho Kenkyu Hokoku, 10, 49-52 (1957). (Abstract in English only). 1 pg.
Han Xiu-Ying et al, Shanxi Daxue Xuebao Bianjibu, 2002, 25(4), 379-80. (Abstract in English only), 1 pg.
Semendyaeva et al, 1981. Khimicheskaya Promyshlennost, Seriya: Khomaya Promyshlennost, 5. 21-2 (CA Summary). XP 002465275, 1 pg.
Rudnenko, EV, et al., 1988, Lakokrasochnye Materially i 1kh Primenenie, 4 69-71 (CA Summary) XP 002465276, 1 pg.
Kirk-Othmer Encyclopedia of Chemical Technology, 1978, 3rd Ed., vol. 4, Blood, Coagulants and Anticoagulants to Cardiovascular Agents. p. 847-848.
Jeffrey Lutje Spelberg, et al, A Tandem Enzyme Reaction to Produce Optically Active Halohydrins, Epoxides and Diols, Tetrahedron: Asymmetry, Elsevler Science Publishers, vol. 10, No. 15, 1999, pp. 2863-2870.
Oleoline.com. Glycerine Market report, Sep. 10, 2003, No. 62, 31 pgs.
Notification Under Act. No. 100/2001, Coll. as Amended by Act. No. 93/2004, Coll. to the extent of Annex No. (SPOLEK) Nov. 30, 2004, 80 pgs.
Documentation Under Act. No. 100/2001 Coll. as Amended by Act. No. 93/2004 Coll in the scope of appendix No. 4 (SPOLEK) Jan. 11, 2005, 86 pgs.
K. Weissermel & H.J. Arpe, Industrial Organic Chemistry, Third, Completely Revised Edition, VCH, 1997, pp. 149 & 275.
Industrial Bioproducts: "Today and Tomorrow." Energetics, Inc. for the U.S. Department of Energy, Office of Energy Efficiency and Renewable Energy, Office of the Biomass Program, Jul. 2003, pp. 49, 52 to 56.
Kirk Othmer Encyclopedia of Chemical Technology, Fourth Edition, 1992, vol. 2, p. 156, John Wiley & Sons, Inc.
Ullmann's Encyclopedia of Industrial Chemistry, Fifth, Completely Revised Edition, 1988, vol. A13, pp. 292-293.
The Merck Index, Eleventh Edition, 1989, pp. 759-760.
Ullmann's Encyclopedia of Industrial Chemistry, Fifth completely Revised Edition, vol. A1, 1985, pp. 427-429.
Ullmann's Encyclopedia of Industrial Chemistry, Fifth Completely Revised Edition, vol. A6, 1986, pp. 240-252.
Hancock, E.G., Propylene and its Industrial Derivatives, 1973, pp. 298-332.
K. Weissermel & H.J. Arpe, Industrial Organic Chemistry, Third, Completely Revised Edition, VCH 1997, pp. 149-163.
K. Weissermel & H.J. Arpe, in Industrial Organic Chemistry, Third, Completely Revised Edition, VCH 1997, pp. 275-276.
Robert T. Morrison & Robert N. Boyd, Organic Chemistry, 5th Ed., vol. II, pp. 666 to 667 and 712 to 714 (Japanese Translation), published on Jul. 10, 1970, Tokyo Kagaku Dozin Co., Ltd. (and similar passages but retrieved from the English Fifth Edition of the Book, 1987).
Perry's Chemical Engineers' Handbook, Sixth Edition, Robert H. Perry, Don Green, 1984, Section 21-64 to 21-68.
Iwanami et al, Dictionary of Physics and Chemistry, Third Edition, Ryo Midorikawa /Iwanami Shoten, Publishers, May 29, 1971, pp. 270-271, 595 and 726.
Expert Opinion on the Environment Impact Assessment Documentation Pursuant to Annex No. 5 of Act No. 100/2001 Coll., as amended by later regulations of the project/intent combined process for the manufacture of epichlorohydrin (SPOLEK) Apr. 2005.
Kirk Othmer Encyclopedia of Chemical Technology, Third Edition, vol. 12, 1980, pp. 1002-1005.
Chemical Engineering Handbook, the 6th Edition, Edited by the Society of Chemical Engineers, published by Maruzen Co, Ltd., 1999, pp. 1296-1306 Pub. Feb. 25, 1999 w/English translation of p. 1296, Table 28.4, p. 1298, left column, lines 4-13 and p. 1305, Table 28.10.
Product Brochure of De Dietrich Company, Apr. 1996, pp. 3, 8 and 9 w/English translation of p. 8, left column, lines 1-4, p. 9.

The Journal of the American Chemical Society, vol. XLV, Jul.-Dec. 1923, pp. 2771-2772.
Berichte Der Deutschen Chemischen Gesellschaft, 1891, vol. 24, pp. 508-510.
Catalogue of Nittetu Chemical Engineering Ltd. (Published in Mar. 1994).
12093 Chemicals, The Chemical Daily Co., Ltd. (Published on Jan. 22, 1993) with attached English translation of relevant excerpts, 24 pgs.
Chemicals Guide, Chemical Daily Co., Ltd. (Published on Jun. 15, 1990) with attached English translation of relevant excerpts.
J.B. Conant, et al, "Glycerol a,y-dichlorohydrin", Organic Syntheses Coll., 1941, vol. 1, p. 292-294 (5 pp.).
Gilman H., Organic Synthesis, Section 1, pp. 234-235 (no date)—attached English translation only.
Industrial Chemical Encyclopedia 5, p. 457 (no date)—attached English translation only.
"Epoxy resins", p. 36-46, by Shangai Resin Plant, Shangai People's Press, 1971—attached English translation only.
Martinetti, R. et al. "Environnement Le Recyclage du l'eau" Industrie Textile, Ste Sippe Sarl, Metz, FR, No. 1300 (Jul. 1, 1998), ISSN: 0019-9176 (no English abstract available)—8 pp.
"Rainwater Harvesting and Utilization" (United Nations Environment Program) Mar. 2002; XP003003726; Internet Citation extracted online on Jan. 1, 2006: URL:http://www.unep.or.ip/letc/Publication—4 pp.
Myszkowski, J. et al. "Removal of chlorinated organic impurities from hydrogen chloride"; English Chemical Abstract summary only of Polish Patent No. 136598 B2 (Mar. 31, 1986); XP002352444; 1 pp.
Myszkowski, J. et al. "Removal of organic compounds from gaseous hydrogen chloride by an absorption method" Chemia Stosowana (1986) vol. 30(4) p. 545-51; English Chemical Abstract Summary only; XP002352445; 1 pp.
Milchert, E. et al. "Recovering hydrogen chloride and organic chloro compounds from the reaction mixture in the chlorination of ethylene"; English Chemical Abstract Summary only of Polish Patent No. 162910 B1 (Jan. 31, 1994); XP002352443; 1 pp.
Laine, D.F. et al. "The destruction of organic pollutants under mild reaction conditions; A review" Michochemical Journla, vol. 85, No. 2, 2007 pp. 183-193; available online Aug. 17, 2006; 12 pp.
U.S. Appl. No. 12/681,083, filed Mar. 31, 2010, Bobet, et al.
[Unknown Author], Kirk Othmer Encyclopedia of Chemical Technology—vol. 2, p. 156, John Wiley and Sons, 1992.
U.S. Appl. No. 12/745,802, Patrick, Gilbeau, et al.
Ullmann's Encyclopedia of Industrial Chemistry, 2005, "pH Measurement and Control", Wiley-VCH GmbH & Co. KGaA, Weinheim, 10.1002/14356007.e19_e01; pp. 1-31 (32 pgs).
Ma Zengxin et al, "recovery of Polyglycerol from residues of Synthetic Glycerol" Riyong Huaxue Gongye, 1997, 4, 21023 (English Abstract only).
San Hee Lee et al. "Direct preparation of Dichloropropanol (DCP) from Glycerol Using Heteropolyacid (HPA) Catalysts: A Catalyst Screen Study," Catalysis Communications (9), 2008, p. 1920-1923.
Production and Prospect of the World Nature Glycerol by Zhu Shiyon, Cereals and Oils, vol. 1, 1997, pp. 33-38 (No English Translation).
Vinnolit: Vinnolit receives EU grant for water recycling project; Press Release, 2008: http://www.vinnolit.de/vinnolit.nsf/EN_Vinnolit_receives_EU_grant_for_water_recycling_project_.
N.W. Ziels, Journal of American Oil Chemists' Society, Nov. 1956, vol. 33, pp. 556-565.
Perry's Chemical Engineers Handbook, Sixth Edition, McGraw Hill Inc., (1984) Section 18.
vol. 83: Unit Operations II of Ullmann's Encyclopedia of Industrial Chemistry, Fifth Completely Revised Edition, Published by VCH, 1988.
W. Giger et al., "14C/12C-Ratios in Organic Matter and Hydrocarbons Extracted from Dated Lake Sediments," Nuclear Instruments and Methods in Physics Research B5 (1984), 394-397, XP-002631954.
Jurgen O. Metzger, "Fats and Oils as Renewable Feedstock for Chemistry," Eur. J. Lipid Sci. Technol. (2009), 111, 865-876, XP-002631953.
Bruce M. Bell, "Glycerin as a Renewable Feedstock for Epichlorohydrin Production. The GTE Process," Clean-Soil, Air, Water, vol. 36, No. 8, (2008) pp. 657-661, XP-002631952.
Horsley, Lee H.—"Azeotropic Data-III", The Dow Chemical Co., Midland, MI, American Chemical Society 1973, pp. 1-4; 4 pgs.
Suzawa, Yoshikazu, et al—"Incineration System for Waste Liquid Containing Chlorinated Organic Compounds", Chemical Apparatuses, 1981, vol. 23, No. 11; 34 pgs; Translation in English provided.
D'Alonzo, R.P., et al—"Glyceride Composition of Processed Fats and Oils as Determined by Glass Capillary Gas Chromatography", Journal of American Oil Chemists' Society, 1982, vol. 59, No. 7, pp. 292-295; 4 pgs.
Chemical Engineering Handbook, $6^{th}$ Revised Edition, 2001, pp. 1-36; 56 pgs; Translation of English provided.
"Electrolytic cell test for electrolysis of epoxy sewage salt to prepare chlor-alkali", Process Equipment Department of Research Institute of Chloro-Alkali, Shengyang Chemical Plant, Liaoning Chemical Industry, Issue n2, pp. 32-37, published Dec. 31, 1981; 17 pgs; Translation of English provided.
Chengxin, Ren, et al—"Analysis on the Composition of the Byproduct During the Manufacturing Process of 3-Epichlorohydrin by GC-MS", Chemical Analysis and Meterage, 2003, vol. 12, Issue No. 3, pp. 25-26; 6 pgs; Translation in English provided.
Encyclopedia of Chemical Technology, vol. 5, Nov. 1993; 6 pgs; Translation in English provided.
"Manufacture and use of epoxy resin", edited by Shanghai Resin Factory, published by China Petrochemical Press, First Edition, Oct. 1974; 16 pgs; Translation in English provided.
Gilman, Henry, et al—"Organic synthesis", Part 1, published by Scientific Publishing, 1957 (with abstract); 4 pgs.
Handbook of Chemical Products, Heavy Organic Chemicals, Second edition, published by Chemical Industry Press, Jan. 1995; 13 pgs; Translation in English provided.
Kiseleva, R. A., et al—"Study of the Interaction of Dibasic Acids with Glycerol", J. App. Chem. USSR, 1971, vol. 44, p. 2086-2090; 5 pgs.
Handbook of Corrosion Data and Material Selection, published by Chemical Industry Press, edited by Jingyi Zuo, Yu Zuo; First edition, Oct. 1995, 5 pgs; Translation in English provided.
Handbook of Azeotropic Mixture, edited by Information Department of Comprehensive Scientific Technology Research Institution of Fushun City, 1993; 8 pgs; Translation in English provided.
"Industry Chemical Reaction and Application", published by Chinese Scientific Technology University Press, 1999; 4 pgs, Translation in English provided.
"Epoxy resin", published by Shanghai People's Publishing House, 1971; Translation in English provided; 21 pgs.
Boschan, Robert, et al—"The Role of Neighboring Groups in Replacement Reactions. XXI. Front-side Participation of Acetoxy Group. Catalytic Effect of Acetic Acid on the Reaction of Glycols with Hydrogen Chloride", Journal of the American Chemical Society, 1956, vol. 78, pp. 4921-4925; 5 pgs.
Encyclopedia for Chinese Adult Education, 1994, p. 623; 10 pgs; Translation in English provided.

* cited by examiner

AQUEOUS COMPOSITION CONTAINING A SALT, MANUFACTURING PROCESS AND USE

CROSS-REFERENCE TO RELATED APPLICATIONS

The present patent application is a U.S. national stage application under 35 U.S.C. §371 of International Application No. PCT/EP2008/057245 filed Jun. 11, 2008, which claims the benefit of the European patent application No. EP 08150927.5 filed on Jan. 31, 2008 and of the French patent application No. FR 07/55697 filed on Jun. 12, 2007, the content of these applications being incorporated herein by reference for all purposes.

The present invention relates to an aqueous composition containing a salt, to a process for its manufacture and to its use in various applications. The invention relates more specifically to a purified saline aqueous composition.

One of the uses of brine or saline aqueous compositions is as a reactant in electrolysis processes (Ullmann's Encyclopedia of Industrial Chemistry, Fifth Completely Revised Edition, Vol. A6, pp. 401-477). In these processes, the salt is of natural origin and comes from a halite mineral, from salt marshes or is obtained by evaporation of brines that originate from mines or from sea water.

U.S. Pat. No. 3,954,581 discloses a process for manufacturing chlorine by electrolysis of a brine wherein a hydroxycarboxylic acid, a phosphorus containing compound and a surfactant are added to the cell in order to lower the hydrogen overpotential in the cell cathodic chamber. The electrolysis cell is a diaphragm cell.

JP patent 09299953 discloses a membrane electrolysis cell which can be fed with a diluted brine containing acetic acid in order to produce a solution suitable for disinfection. Such a brine is not suitable for a commercial chlorine production.

The purpose of the present invention is to provide a new aqueous composition containing a salt which is suitable for a commercial chlorine production.

The invention hence relates to an aqueous composition containing at least one salt in an amount of at least 30 g/kg of composition, of which the total organic carbon content is at least 1 μg of C/l and at most 5 g of C/l of composition and which contains at least one carboxylic acid.

One of the essential characteristics of the invention resides in that when the salt in the brine is not of natural origin and when the brine is contaminated by various organic compounds, it can nevertheless be used as a raw material in electrolysis processes. It has been found that it is possible to tolerate the presence of a carboxylic acid and of a high total organic carbon (TOC) content in the aqueous composition to be electrolyzed. It has indeed surprisingly been found that such characteristics do not affect the performances of the electrolysis process. In particular, the expected reduction of the yield of the electrolysis process due to secondary electrode reactions, electrode overplating, increased overpotentials, foaming, membrane or diaphragm fouling, etc. are not observed. That yield can even be increased.

In the next part of the description, the aqueous composition according to the invention will also be referred to as the brine according to the invention or simply as the brine.

In the aqueous composition of the invention, the total organic carbon content is often at most 3 g C/l, frequently at most 2 g C/l, more often at most 1 g C/l, often at most 0.1 g C/l, even more often at most 0.05 g C/l, still more frequently at most 0.01 g C/l and most particularly at most 0.005 g C/l. A total organic carbon content of less than 0.001 g C/l is particularly suitable and a total organic carbon content of less than 0.5 mg C/l is most particularly suitable.

In the aqueous composition according to the invention, the carboxylic acid may be a monocarboxylic acid, a polycarboxylic acid, or a mixture thereof. The polycarboxylic acids can be selected from dicarboxylic acids, tricarboxylic acids, tetracarboxylic acids, and any mixture of at least two of them. Dicarboxylic acids are more often encountered.

In the aqueous composition according to the invention, the carboxylic acid generally comprises from 1 to 10 carbon atoms, often from 1 to 5 carbon atoms frequently from 1 to 3 carbon atoms and specifically from 1 to 2 carbon atoms. The carboxylic acid may optionally be substituted, for example by a hydroxy group or a chloride. Often, the acid may be chosen from formic acid, acetic acid, propionic acid, glycolic (hydroxyacetic) acid, lactic (2-hydroxypropanoic) acid, monochloroacetic acid, dichloroacetic acid, trichloroacetic acid, oxalic acid, succinic acid, adipic acid, glyceric acid, pyruvic acid, and mixtures of at least two of them. Frequently, the carboxylic acid is not a hydroxycarboxylic acid. Most often, the carboxylic acid is formic acid or acetic acid and particularly more frequently formic acid. The carboxylic acid is specifically acetic acid. In the aqueous composition of the invention, the carboxylic acid may be in a protonated form, in a deprotonated form or in a mixture of the two forms, depending on the pH of the aqueous composition.

The carboxylic acid content, expressed in g of carbon per l (litre) of aqueous composition, is usually at most 5 g C/l, commonly at most 3 g C/l, generally at most 2 g C/l, often at most 1 g of C/l, frequently at most 0.1 g of C/l, more often at most 0.05 g of C/l, more frequently at most 0.01 g of C/l and most particularly at most 0.005 g of C/l. Such a content of less than 0.001 g of C/l is particularly suitable and such a content of less than 0.5 mg C/l is most particularly suitable. The carboxylic acid content, expressed in g of carbon per l of aqueous composition, is generally at least 1 μg of C/l.

In the aqueous composition according to the invention, the salt content is preferably at least 50 g per kg of aqueous composition, preferably at least 70 g/kg, more preferably at least 100 g/kg, yet more preferably at least 140 g/kg, still more preferably at least 160 g/kg and most preferably at least 200 g/kg. The salt content is usually at most 350 g/kg, commonly at most 325 g/kg, generally at most 270 g/kg, often at most 250 g/kg, and frequently at most 230 g/kg. A salt content of 200 g/kg is particularly convenient.

The aqueous composition may be unsaturated, saturated or super saturated with the salt.

The salts may be chosen from alkali or alkaline-earth metal chlorides, sulphates, hydrogen sulphates, hydroxides, carbonates, hydrogen carbonates, phosphates, hydrogen phosphates, borates, and mixtures thereof. Alkali and alkaline-earth metal halides are preferred. Sodium and potassium chlorides are more preferred and sodium chloride is most particularly preferred.

The aqueous composition according to the invention may contain polyvalent metals. The content of these metals is generally less than or equal to 500 mg per kg of aqueous composition, preferably less than or equal to 300 mg/kg, more preferably less than or equal to 200 mg/kg, yet more preferably less than or equal to 100 mg/kg, still more preferably less than or equal to 10 mg/kg, particularly preferably less than or equal to 0.5 mg/kg, even more preferably less than or equal to 0.1 mg/kg and most particularly preferably less than or equal to 0.02 mg/kg.

When the salt present in the aqueous composition according to the invention is an alkali metal salt, these polyvalent metals are, for example, metals from the families IIA, IVA, VA, VIA, VIIA, IB, IIB and IIIB of the IUPAC nomenclature of the Periodic Table of the Elements, in particular calcium, magnesium, strontium, barium, silicon, lead, cobalt, manganese, aluminium, mercury, iron and nickel.

When the salt present in the aqueous composition according to the invention is an alkaline-earth metal salt, these polyvalent metals are, for example, metals from the families IVA, VA, VIA, VIIA, IB, IIB and IIIB of the IUPAC nomenclature of the Periodic Table of the Elements, in particular, silicon, lead, cobalt, manganese, aluminium, mercury, iron and nickel.

All the following contents of metal are expressed as weight of elements per weight of aqueous composition, except for silicon where the content is expressed in weight of silica per weight of aqueous composition.

In the aqueous composition according to the invention, the sum of the calcium and magnesium contents is generally less than or equal to 0.5 mg/kg, preferably less than or equal to 0.2 mg/kg, more preferably less than or equal to 0.05 mg/kg, and most preferably less than 0.02 mg/kg of aqueous composition. That content is usually higher than or equal to 1 µg/kg.

In the aqueous composition according to the invention, the strontium content is generally less than or equal to 4 mg/kg, preferably less than or equal to 2 mg/kg, more preferably less than or equal to 1 mg/kg, and most preferably less than 0.4 mg/kg. That content is usually higher than or equal to 1 µg/kg.

In the aqueous composition according to the invention, the barium content is generally less than or equal to 5 mg/kg, preferably less than or equal to 2 mg/kg, more preferably less than or equal to 1 mg/kg, and most preferably less than 0.5 mg/kg. That content is usually higher than or equal to 1 µg/kg In the aqueous composition according to the invention, the aluminium content is generally less than or equal to 200 mg/kg, preferably less than or equal to 100 mg/kg, more preferably less than or equal to 50 mg/kg, yet more preferably less than or equal to 10 mg/kg, still more preferably less than or equal to 1 mg/kg and most preferably less than 0.1 mg/kg. That content is usually higher than or equal to 1 µg/kg.

In the aqueous composition according to the invention, the content of heavy metals except barium, strontium and mercury is generally less than or equal to 10 mg/kg, preferably less than or equal to 5 mg/kg, more preferably less than or equal to 2 mg/kg, yet more preferably less than or equal to 1 mg/kg, still more preferably less than or equal to 0.5 mg/kg and most preferably less than 0.2 mg/kg. That content is usually higher than or equal to 1 µg/kg. By heavy metals one intends to designate the group of elements between copper and bismuth in the Periodic Table of the Elements.

In the aqueous composition according to the invention, the content of lead is generally less than or equal to 5 mg/kg, preferably less than or equal to 2 mg/kg, more preferably less than or equal to 1 mg/kg, yet more preferably less than or equal to 0.5 mg/kg, still more preferably less than or equal to 0.1 mg/kg and most preferably less than 0.05 mg/kg. That content is usually higher than or equal to 1 µg/kg.

In the aqueous composition according to the invention, the content of cobalt is generally less than or equal to 5 mg/kg, preferably less than or equal to 2 mg/kg, more preferably less than or equal to 1 mg/kg, yet more preferably less than or equal to 0.5 mg/kg, still more preferably less than or equal to 0.1 mg/kg and most preferably less than 0.01 mg/kg. That content is usually higher than or equal to 1 µg/kg.

In the aqueous composition according to the invention, the content of manganese is generally less than or equal to 5 mg/kg, preferably less than or equal to 2 mg/kg, more preferably less than or equal to 1 mg/kg, yet more preferably less than or equal to 0.5 mg/kg, still more preferably less than or equal to 0.1 mg/kg and most preferably less than 0.01 mg/kg. That content is usually higher than or equal to 1 µg/kg.

In the aqueous composition according to the invention, the content of mercury is generally less than or equal to 10 mg/kg, preferably less than or equal to 5 mg/kg, more preferably less than or equal to 2 mg/kg, yet more preferably less than or equal to 1 mg/kg, still more preferably less than or equal to 0.5 mg/kg and most preferably less than 0.1 mg/kg. That content is usually higher than or equal to 1 µg/kg.

In the aqueous composition according to the invention, the content of nickel is generally less than or equal to 10 mg/kg, preferably less than or equal to 5 mg/kg, more preferably less than or equal to 2 mg/kg, yet more preferably less than or equal to 1 mg/kg, still more preferably less than or equal to 0.2 mg/kg, particularly more preferably less than or equal to 0.1 mg/kg and most preferably less than 0.01 mg/kg. That content is usually higher than or equal to 1 µg/kg.

In the aqueous composition according to the invention, the iron content is generally less than or equal to 10 mg/kg, preferably less than or equal to 5 mg/kg, more preferably less than or equal to 2 mg/kg, yet more preferably less than or equal to 1 mg/kg, still more preferably less than or equal to 0.2 mg/kg and most preferably less than 0.1 mg/kg. That content is usually higher than or equal to 1 µg/kg.

In the aqueous composition according to the invention, the silicon content is generally less than or equal to 50 mg of $SiO_2$/kg, preferably less than or equal to 20 mg/kg, more preferably less than or equal to 10 mg/kg and most preferably less than 5 mg/kg. That content is usually higher than or equal to 1 µg/kg.

The aqueous solution of the invention may also contain ammonium. The ammonium content is generally less than or equal to 10 mg of ammonium (expressed as $NH_4$)/kg, preferably less than or equal to 5 mg/kg, more preferably less than or equal to 1 mg/kg and most preferably less than 0.5 mg/kg. By ammonium one intends to designate ammonium ion, ammonia and mixtures thereof. That content is usually higher than or equal to 0.1 mg/kg.

The aqueous composition of the invention may also contain halogens i.e., fluorine, chlorine, bromine and iodine.

In the aqueous composition according to the invention, the fluorine content is generally less than or equal to 50 mg of fluorine (expressed as $F_2$)/kg, preferably less than or equal to 20 mg/kg, more preferably less than or equal to 10 mg/kg and most preferably less than 1 mg/kg.

In the aqueous composition according to the invention, the bromine content is generally less than or equal to 500 mg of bromine (expressed as $Br_2$)/kg, preferably less than or equal to 200 mg/kg, more preferably less than or equal to 100 mg/kg and most preferably less than 50 mg/kg.

In the aqueous composition according to the invention, the iodine content is generally less than or equal to 50 mg of iodine (expressed as $I_2$)/kg, preferably less than or equal to 20 mg/kg, more preferably less than or equal to 10 mg/kg and most preferably less than 1 mg/kg.

By fluorine, iodine and bromine, one intends to designate the various existing inorganic species containing at least one fluorine atom or one iodine atom or one bromine atom, e.g., fluoride, fluorine, and mixtures thereof, or iodide, iodine, hypoiodous, iodate, and mixtures thereof, or bromide, bromine, hypobromous, bromate, and mixtures thereof.

The aqueous composition according to the invention may contain active chlorine. The expression "active chlorine" is understood to mean molecular chlorine and its reaction products with water or with a basic agent, such as hypochlorous acid and sodium hypochlorite for example. The active chlorine content in the aqueous composition is generally greater than or equal to 0.001 mg $Cl_2$/kg of aqueous composition, preferably greater than or equal to 0.01 mg/kg and more preferably greater than or equal to 0.1 mg/kg. This content is generally less than or equal to 10 g $Cl_2$/kg of aqueous composition, usually of less than 5 g $Cl_2$/kg, more generally less than or equal to 1 g/kg, preferably less than or equal to 0.1 g/kg and more preferably less than or equal to 0.01 g/kg.

The aqueous composition according to the invention may also contain chlorate. The chlorate content in the aqueous composition is generally greater than or equal to 1 mg $ClO_3$/kg of aqueous composition, often greater than or equal to 10 mg/kg and frequently greater than or equal to 100 mg/kg. This content is generally less than or equal to 15 g $ClO_3$/kg of aqueous composition, often less than or equal to 10 g/kg and frequently less than or equal to 5 g/kg. By chlorate one intends to designate chlorate ion, chloric acid ($HClO_3$) and mixtures thereof.

Besides carboxylic acids, the aqueous composition according to the invention may also contain other organic compounds. Such organic compounds are for example ketones, aldehydes, alcohols, epoxides, chloroalcohols, chlorinated hydrocarbons, ethers and any mixture of at least two of them.

Examples of ketones are acetone, 2-butanone, cyclopentanone, chloroacetone, hydroxyacetone (acetol), and any mixture of at least two of them.

Examples of aldehydes are acrolein, glyceraldehyde, formaldehyde, acetaldehyde, propionaldehyde, butyraldehyde and any mixture of at least two of them.

Examples of epoxides are epichlorohydrin, 2,3-epoxy-1-propanol (glycidol), and mixtures thereof.

An example of halogenated hydrocarbons is 1,2,3-trichloropropane.

Examples of alcohols are isopropanol, phenol, glycerol, and any mixtures of at least two of them.

Examples of chloroalcohols are 2-chloro-2-propen-1-ol, 3-chloro-2-propen-1-ol cis, 1-methoxy-3-chloropropane-2-ol, 3-chloro-1-propane-1-ol, 3-chloro-2-propen-1-ol trans, 1,3-dichloro-2-propanol, 2,3-dichloro-1-propanol, 1-chloro-2,3-propanediol, 2-chloro-1,3-propanediol, and any mixtures of at least two of them.

Examples of ethers are cyclic diglycerols.

Organic compounds of crude formula $C_6H_{12}O$, $C_6H_8O_2$, $C_6H_{12}OCl_2$, $C_6H_{10}O_2Cl_2$, $C_9H_{10}O_2$, and any mixture of at least two of them may also be present in the aqueous composition according to the invention.

The invention also relates to a process for manufacturing the aqueous composition according to the invention, comprising the following steps:
a) in a liquid reaction medium, a mixture of dichloropropanol containing 1,3-dichloro-2-propanol and 2,3-dichloro-1-propanol, in which the 1,3-dichloro-2-propanol content, relative to the sum of the 1,3-dichloro-2-propanol and 2,3-dichloro-1-propanol contents, is at least 10% by weight, is reacted with at least one basic compound in order to form epichlorohydrin and at least one salt;
b) at least one part of the liquid reaction medium from step a) is subjected to a settling operation in which a first fraction containing most of the epichlorohydrin which was contained in the part of the reaction medium from step a) before the settling operation is separated from a second fraction containing most of the salt which was contained in the part of the reaction medium from step a) before the settling operation; and
c) the second fraction separated in step b) is subjected to at least one treatment selected from a physical treatment, a chemical treatment, a biological treatment, and any combination thereof.

The physical treatment may be chosen from dilution, concentration, evaporation, distillation, stripping, liquid/liquid extraction, filtration and adsorption operations, alone or in combination.

The chemical treatment may be chosen from oxidation, reduction, neutralization, complexation and precipitation operations, alone or in combination.

The biological treatment may be chosen from an aerobic and an anaerobic bacterial treatment, alone or in combination. The bacteria may be free (activated sludge, lagooning) or fixed (trickling filter, planted filters, sand filters, bio filter) or else biodiscs.

In the rest of the document, the expression "most of" is understood to mean "half and more than half of" i.e., 50% by weight or more than 50% by weight.

Steps a) and b) of the process used to manufacture the product according to the invention may be carried out under conditions such as those described in Applications FR 07/53375 and FR 07/55448 in the name of Solvay SA. The liquid reaction medium from step a) may especially contain an organic solvent, such as 1,2,3-trichloropropane for example.

The liquid reaction medium from step a) before the settling operation of step b) comprises epichlorohydrin in a content usually higher than or equal to 70 g of epichlorohydrin per kg of liquid reaction medium, often higher than or equal to 100 g/kg, frequently higher than or equal to 150 g/kg and specifically higher than or equal to 175 g/kg. That epichlorohydrin content is usually lower than or equal to 460 g of epichlorohydrin per kg of liquid reaction medium, often lower than or equal to 300 g/kg, frequently lower than or equal to 275 g/kg and specifically lower than or equal to 250 g/kg.

The liquid reaction medium from step a) may contain some solid, for instance the salt produced at step a) of the process according to the invention.

Steps a) to c) of the process for obtaining the aqueous composition according to the invention may independently be carried out in continuous or batch mode. It is preferred to carry out steps a) to c) in continuous mode.

In the process according to the invention, the reaction from step a) may be carried out in one or more reaction zones.

In the process according to the invention, the reaction zones may be supplied independently of one another with dichloropropanol, with the basic compound, with water or with at least two of these compounds.

In the process according to the invention, the salt included in the second fraction separated in step b) may be an organic or inorganic salt. Inorganic salts are preferred. The expression "inorganic salts" is understood to mean salts whose constituent ions do not contain a carbon-hydrogen bond.

In the process according to the invention, the second fraction separated in step b) generally comprises water. The water content is generally at least 500 g of water per kg of second fraction, preferably at least 600 g/kg, more preferably at least 700 g/kg and more particularly preferably at least 750 g/kg. The water content is generally at most 990 g of water per kg of second fraction, preferably at most 950 g/kg, more preferably at most 900 g/kg and more particularly preferably at most 850 g/kg.

In the process according to the invention, the second fraction separated in step b) generally comprises at least 50 g of salt/kg, preferably at least 100 g of salt/kg, more preferably at least 150 g of salt/kg and most particularly preferably at least 200 g of salt/kg. Most particularly, the salt concentration is below the solubility limit of the salt in this second fraction.

The salt present in the second fraction separated in step b) of the process according to the invention is preferably chosen from alkali and alkaline-earth metal chlorides, sulphates, hydrogen sulphates, hydroxides, carbonates, hydrogen carbonates, phosphates, hydrogen phosphates and borates, and mixtures thereof. A portion of this salt cannot be produced in the course of the reaction between dichloropropanol and the basic agent during step a) of the process according to the invention. This salt may thus be present in the reactants, for example. The term "reactants" is understood to mean dichloropropanol and the basic agent. The salt may also be added to step a) or to step b) of the process according to the invention, before the settling operation. Preferably, this salt is partly formed in the reaction of step a) and is partly present in the basic agent.

In the process according to the invention, the second fraction may contain organic compounds. The latter may come from the dichloropropanol manufacturing process and/or be formed during the reaction between dichloropropanol and the basic compound during step a) of the process according to the invention. Examples of these compounds are acetone, acrolein, 2-butanone, isopropanol, 3-methoxy-1,2-epoxypropane, cyclopentanone, epichlorohydrin, chloroacetone, hydroxyacetone (acetol), $C_6H_{12}O$, 1,2,3-trichloropropane, 2,3-epoxy-1-propanol (glycidol), 2-chloro-2-propen-1-ol, 3-chloro-2-propen-1-ol cis, 1-methoxy-3-chloropropane-2-ol, 3-chloro-1-propane-1-ol, 3-chloro-2-propen-1-ol trans, $C_6H_8O_2$, $C_6H_{12}OCl_2$, $C_6H_{10}O_2Cl_2$, 1,3-dichloro-2-propanol, $C_9H_{10}O_2$, 2,3-dichloro-1-propanol, phenol, glycerol, 1-chloro-2,3-propanediol, 2-chloro-1,3-propanediol, cyclic diglycerols, glyceraldehyde, formaldehyde, acetaldehyde, propionaldehyde, butyraldehyde, acetic acid, propionic acid, formic acid, glycolic acid, oxalic acid, lactic acid, and mixtures thereof.

The epichlorohydrin content of the second fraction separated in step b) is generally at least 0.1 g/kg of second fraction, preferably at least 1 g/kg, more preferably at least 5 g/kg and most particularly preferably at least 10 g/kg. This content does not generally exceed 60 g/kg, preferably 50 g/kg, even more preferably 40 g/kg and most particularly preferably 35 g/kg.

The sum of the 1,3-dichloro-2-propanol and 2,3-dichloro-1-propanol contents of the second fraction separated in step b) is generally at least 0.1 g/kg of second fraction, preferably at least 1 g/kg and more preferably at least 2 g/kg. This sum is generally at most 100 g/kg, preferably at most 80 g/kg and even more preferably at most 40 g/kg.

The sum of the 3-chloro-1,2-propanediol and 2-chloro-1,3-propanediol contents of the second fraction separated in step b) is generally at most 50 g/kg of second fraction, preferably at most 10 g/kg and even more preferably at most 1 g/kg. This sum is generally at least 0.1 g/kg.

In the process according to the invention, the second fraction separated may contain a basic compound, preferably an inorganic basic compound.

This inorganic basic compound may be chosen from alkali or alkaline-earth metal oxides, hydroxides, carbonates, hydrogen carbonates, phosphates, hydrogen phosphates and borates, and mixtures of at least two of them. The inorganic basic compound content is generally at least 0.005 g/kg of second fraction, preferably at least 0.05 g/kg, more preferably at least 0.1 g/kg of second fraction, preferably at least 0.5 g/kg, and more preferably at least 1 g/kg. This content is generally at most 25 g/kg of second fraction, preferably at most 10 g/kg, and more preferably at most 5 g/kg.

The total organic carbon (TOC) content of the second fraction separated in step b) is generally at most 40 g of carbon/l of second fraction separated in step b) and frequently at most 16 g of carbon/l and usually at most 13 g of carbon/l.

In a first embodiment of the process for manufacturing the aqueous composition according to the invention, the treatment from step c) is a physical treatment and comprises at least one operation selected from evaporation, distillation, stripping operation and combinations thereof.

In a first variant of the first embodiment, the treatment comprises an evaporation operation. The term "evaporation" is understood to mean the separation of a substance by heating, optionally under reduced pressure. The temperature of the second fraction separated in step b) entering the evaporation operation is generally at least 10° C., usually at least 30° C., frequently at least 40° C. and more specifically at least 45° C. This temperature is generally at most 200° C., usually at most 160° C., frequently at most 150° C. and more specifically at most 140° C.

The evaporation operation may be carried out using any equipment such as, for example, a still, a natural circulation, rising film, falling film or rising and falling film or forced circulation tubular evaporator, or a plate evaporator. The temperature of the "foot" of the evaporator is generally at least 10° C., usually at least 30° C., frequently at least 40° C. and more specifically at least 45° C. This temperature is generally at most 200° C., usually at most 160° C., frequently at most 150° C. and more specifically at most 140° C.

In this first variant, the evaporation may be carried out under a pressure of 1 bar absolute, under a pressure above 1 bar absolute or under a pressure below 1 bar absolute. The evaporation may be carried out under a pressure of at most 5 bar absolute, preferably at most 3 bar absolute and more preferably at most 2 bar absolute. This pressure is generally at least 15 mbar absolute, usually at least 35 mbar, frequently at least 55 mbar, more frequently at least 150 mbar and more specifically at least 350 mbar.

In a second variant of the first embodiment, the treatment comprises a distillation operation. The term "distillation" is understood to mean the direct transition from the liquid state to the gas state, then condensation of the vapours obtained. The term "distillation" is preferably intended to denote the type of separation conventional in chemical engineering and described, for example, in "Perry's Chemical Engineers' Handbook" in the 13th section of the 7th edition, 1997.

The term "fractional distillation" is understood to mean a series of distillations carried out on the successively condensed vapours. The term "fractional distillation" is preferably understood to mean a sequence of distillations where the distillate is withdrawn batchwise.

In this second variant, the temperature of the second fraction separated in step b) entering the distillation step is generally at least 10° C., usually at least 30° C., frequently at least 40° C. and more specifically at least 45° C. This temperature is generally at most 200° C., usually at most 160° C., frequently at most 150° C. and more specifically at most 140° C.

In this second variant, the distillation may be carried out under a pressure of 1 bar absolute, under a pressure above 1 bar absolute or under a pressure below 1 bar absolute. The distillation may be carried out under a pressure of at most 5 bar absolute, preferably at most 3 bar absolute and more preferably at most 2 bar absolute. This pressure is generally at least 15 mbar absolute, usually at least 35 mbar, frequently at least 55 mbar, more frequently at least 150 mbar and more specifically at least 350 mbar.

The distillation operation may be carried out using any equipment such as, for example, a conventional plate column or a "dual-flow" type plate column, or else a column with random or structured packing. The temperature of the "foot" of the distillation column is generally at least 10° C., usually at least 30° C., frequently at least 40° C. and more specifically at least 45° C. This temperature is generally at most 200° C., usually at most 160° C., frequently at most 150° C. and more specifically at most 140° C.

In this second variant, the distillation operation may be carried out in the presence or absence of a gas flow. It is preferred to carry out the distillation without a gas flow, at a total pressure above atmospheric pressure.

In a third variant of the first embodiment, the treatment comprises a stripping operation. The term "stripping" is understood to mean the separation of a substance by the entrainment using the vapour of a pure material that does or does not dissolve this substance. In the process according to the invention, this material can be any compound which is inert with respect to epichlorohydrin, such as, for example, steam, air, nitrogen, combustion gases and carbon dioxide. The combustion gases comprise at least two compounds chosen from water, carbon oxides, nitrogen oxides and sulphur oxides. It is preferred to use nitrogen or steam, preferably steam.

In this third variant, the temperature of the second fraction separated in step b) submitted to the stripping operation is generally at least 10° C., usually at least 30° C., frequently at least 40° C. and more specifically at least 45° C. This temperature is generally at most 200° C., usually at most 160° C., frequently at most 150° C. and more specifically at most 140° C.

In this third variant, the stripping may be carried out under a pressure of 1 bar absolute, under a pressure above 1 bar absolute or under a pressure below 1 bar absolute. The stripping may be carried out under a pressure of at most 5 bar absolute, usually at most 3 bar and frequently at most 2 bar. This pressure is generally at least 15 mbar absolute, usually at least 35 mbar, frequently at least 55 mbar, more frequently at least 150 mbar and more specifically at least 350 mbar.

The stripping operation may be carried out with an external supply of heat or adiabatically. The external supply of heat may be live steam injected directly into the separated second fraction or exchanged using a steam exchanger. The injection of live steam is preferred. The stripping operation may be carried out in a column that brings the separated second fraction into contact with a gas phase or by expansion in a device dispersing the liquid in small droplets (spray nozzle) and producing a VMD (volume mean diameter) less than or equal to 6 mm, preferably less than or equal to 3 mm and more particularly less than or equal to 2 mm. When the stripping operation is carried out in a column, the column may be a plate column (any type of plates) or a column with random or structured packing, preferably a packed column, and more particularly a column with random packing. When the stripping is carried out with steam in a column, the pressure is preferably greater than or equal to 0.5 bar absolute and more particularly greater than or equal to 0.7 bar absolute. This pressure is preferably less than or equal to 5 bar absolute, more particularly less than or equal to 2 bar absolute, and most particularly less than or equal to 1.5 bar absolute. When the stripping is carried out by a gas, the gas is preferably air or hot combustion gases, and more preferably air. The pressure is preferably greater than or equal to 0.9 bar absolute, and preferably less than or equal to 5 bar absolute. When the stripping is carried out by expansion, the expansion is preferably adiabatic and preferably takes place in the absence of a third gas. This expansion is carried out at a pressure preferably greater than or equal to 0.05 bar absolute, more preferably greater than or equal to 0.1 bar absolute and most particularly preferably greater than or equal to 0.15 bar absolute. This pressure is preferably less than or equal to 1.5 bar absolute, more preferably less than or equal to 1 bar absolute and most particularly preferably less than or equal to 0.7 bar absolute. Before expansion, the liquid is reheated via an exchanger or by injection of live steam, preferably by injection of live steam.

In the first embodiment of the process according to the invention, recovered at the end of the treatment from step c) is a first part containing most of the epichlorohydrin and dichloropropanol which were contained in the second fraction separated before the treatment from step c). This first part may also contain light organic compounds, that is to say, organic compounds having boiling points below that of epichlorohydrin, such as acrolein, and heavy organic compounds, that is to say, organic compounds having boiling points between that of epichlorohydrin and of dichloropropanol, such as glycidol and 2-chloro-2-propen-1-ol, and products forming an azeotropic mixture with water such as for instance phenol.

This first part may be subjected to one or more supplementary distillation operations in order to separate the various constituents such as described in the French patent application FR 07/55696 entitled "Epichlorohydrin, manufacturing process and use" filed in the name of Solvay SA on Jun. 12, 2007.

This first part may also be recycled to step a) of the process according to the invention.

In the first embodiment of the process according to the invention, recovered at the end of the treatment from step c) is a second part which forms the aqueous composition according to the invention and which contains water, salt, epichlorohydrin, dichloropropanol, super-heavy organic compounds, that is to say, ones having boiling points above that of dichloropropanol, as well as a reduced fraction of the organic compounds present in the first part. The total organic carbon content of this second part is less than 5 gC/l, preferably less than 1 gC/l. The salt content is higher than or equal to 30 g/kg. The second part comprises at least one carboxylic acid.

In a second embodiment of the process for manufacturing the product according to the invention, the treatment from step c) is a physical treatment and comprises at least one adsorption operation. The adsorbent may be chosen from ion-exchange resins, celluloses, starch gels, inorganic adsorbents such as aluminas, silicas, zeolites and exchanged zeolites, polymer resins, such as macroporous crosslinked polystyrene for example, activated carbons and resins grafted with boronic acid groups. Activated carbons are preferred. Activated carbon may be obtained from natural or synthetic raw materials. Examples of natural raw materials are nutshell, coconut shell, wood, and coal. Examples of synthetic raw materials, are polymers like polyvinyl alcohol. Examples of commercial activated carbons are CPG FE90219F, CPG FE02416A, C 1340 from Chemviron. The general objective of this adsorption operation is to eliminate, at least partially, the metals and the halogens other than chlorine, such as bromine and iodine, in particular in the form of complex ions such as bromate and iodate ions.

The adsorption operation is generally carried out at a temperature of at least 10° C., usually at least 15° C., frequently at least 20° C. and more specifically at least 25° C. This temperature is generally at most 160° C., usually at most 120° C., frequently at most 100° C. and more specifically at most 80° C.

In this second embodiment, the adsorption operation may be carried out under a pressure of 1 bar absolute, under a pressure above 1 bar absolute or under a pressure below 1 bar absolute. It is preferred to carry out the adsorption operation under a pressure of at most 10 bar absolute, usually at most 5 bar and frequently at most 2 bar. This pressure is generally at least 0.5 bar absolute, usually at least 0.7 bar, frequently at least 0.9 bar and more specifically at least 1 bar.

In the second embodiment of the process according to the invention, recovered at the end of the treatment from step c) is a first portion which comprises the adsorbent and most of the organic compounds which were contained in the second fraction separated before the treatment from step c) and a second portion which forms the aqueous composition according to the invention and which contains water and salt and at least one carboxylic acid. The salt content is higher than or equal to 30 g/kg. The total organic carbon content of this second part is less than 5 gC/l, frequently less than 1 g C/l.

In a third embodiment of the process for manufacturing the product according to the invention, the treatment from step c) is a physical treatment and comprises at least one liquid/liquid extraction operation.

The extraction solvent is generally an organic solvent which may be chosen from esters, ketones, ethers, alcohols, carboxylic acids and phosphine oxides. The organic solvents may contain water, preferably up to saturation.

The esters may be chosen from the esters of fatty acids such as caproic, oleic, myristic or stearic acid, phthalic, glycolic, adipic, sebacic, and phosphoric acids and any mixture of at least two of them.

The fatty acid esters may be chosen from butyl oleate, methyl myristate, diethylene glycol dilaurate, cyclohexyl stearate, ethyl caproate, methyl octanoate, methyl decanoate, methyl dodecanoate, methyl tetradecanoate, methyl hexadecanoate, methyl octadecanoate and any mixture of at least two of them. The fatty acid esters are preferably mixtures of esters obtained by transesterification of vegetable, animal or fish oils, in particular the methyl or ethyl esters prepared from palm oil, palm kernel oil, coconut oil, babassu oil, rapeseed oil, sunflower oil, maize oil, castor oil, cottonseed oil, arachis oil, soybean oil, linseed oil and sea kale oil, and also all the oils from sunflower or rapeseed plants obtained by genetic modification or hybridization.

The phthalic acid esters may be chosen from diethyl, di-n-butyl, di-n-amyl, di-2-ethylhexyl phthalates, and any mixture of at least two of them.

The glycolic acid esters may be chosen from methyl phthalyl ethyl, ethyl phthalyl ethyl, butyl phthalyl ethyl glycolates and any mixture of at least two often. The adipic acid esters may be chosen from di(2-ethylhexyl), didecyl adipate, and mixtures thereof.

The sebacic acid ester may be di-n-butyl sebacate.

The phosphoric acid esters may be chosen from tributyl phosphate, butyl dioctyl phosphate, tri-n-octyl phosphate, tri(2-ethylhexyl)phosphate, trihexyl phosphate, tridecyl phosphate, trioctadecyl phosphate, tricresyl phosphate, 2-ethyl diphenyl phosphate, cresyl diphenyl phosphate, o-chlorophenyl diphenyl phosphate, bis(p-tert-butylphenyl) phenyl phosphate, and any mixture of at least two of them.

The ketone may be isobutyl heptyl ketone.

The ether may be a monoether such as dihexyl ether or an alkylene glycol diether such as ethylene glycol diethyl ether, ethylene glycol dipropyl ether, ethylene glycol dibutyl ether, ethylene glycol dihexyl ether, diethylene glycol dipropyl ether, diethylene glycol dibutyl ether, diethylene glycol dihexyl ether, propylene glycol diethyl ether, propylene glycol dipropyl ether, propylene glycol dibutyl ether and dipropylene glycol dimethyl ether, dipropylene glycol diethyl ether, butylene glycol diethyl ether, dibutylene glycol diethyl ether, triethylene glycol diethyl ether, tetraethylene glycol diethyl ether, hexaethylene glycol diethyl ether and ethylene glycol ethyl butyl ether, and any mixture of at least two of them.

The alcohols may be monoalcohols, diols or mixtures of monoalcohols and diols.

Among the monoalcohols, dichloropropanol, preferably 2,3-dichloro-propan-1-ol and 1,3-dichloropropan-2-ol, and linear or branched, primary or secondary alcohols containing more than 5 carbon atoms are preferred. These alcohols may be chosen from 1-octanol, nonanol, 5-nonanol, 2,6-dimethyl-4-heptanol, 1-decanol, isodecanol, 1-dodecanol, undecanol, preferably 5-ethyl-2-nonanol, tetradecanol, preferably 1-tetradecanol and 7-ethyl-2-methyl-4-undecanol, 1-hexadecanol, heptadecanol, preferably 3,9-diethyl-6-tridecanol, 1-octadecanol, and any mixture of at least two of them.

The diols may be chosen from 1,2-octanediol, 1,2-decanediol, 1,2-dodecanediol, 1,2-tetradecanediol, and any mixture of at least two of them.

1-Octanol, 1-decanol, 2,3-dichloropropan-1-ol and 1,3-dichloropropan-2-ol and 1,2-dodecanediol are preferred. 1,2-Dodecanediol, 2,3-dichloropropan-1-ol and 1,3-dichloropropan-2-ol are more preferred. 1,3-Dichloropropan-2-ol, 2,3-dichloropropan-1-ol, and mixtures thereof containing at least 50 wt % of 1,3-dichloropropan-2-ol are most preferred. The mixture of the 2 dichloropropanol isomers may be a crude or purified product derived from several processes such as, for example, the allyl chloride hypochlorination process, the allyl alcohol chlorination process and the glycerol hydrochlorination process. In the extraction treatment according to the invention, at least one part of the dichloropropanol is preferably obtained by reaction between glycerol and a chlorinating agent containing hydrogen chloride such as described in Patent Application WO 2005/054167 by Solvay SA. The latter have the advantage of not introducing an external compound into the manufacturing process. Another advantage is that the mixture of the two dichloropropanol isomers separated after the liquid/liquid extraction step can be recycled to step a) of the process according to the invention.

The carboxylic acids are preferably chosen from oleic, linoleic, heptanoic, pelargonic, caproic, caprylic, capric, undecanoic, lauric, stearic, myristic, palmitic, palmitoleic, ricinoleic, cyclohexanecarboxylic acids, and any mixture of at least two of them. The mixtures of fatty acids resulting from the hydrolysis of vegetable, animal or fish oils can also be used, inter alia the mixtures of acids obtained from palm oil, palm kernel oil, coconut oil, babassu oil, rapeseed oil, sunflower oil, maize oil, castor oil, cottonseed oil, arachis oil, soybean oil, linseed oil and sea kale oil, and also all the oils from sunflower or rapeseed plants obtained by genetic modification or hybridization, and the acids obtained by distillation of tall oils, liquid co-products of the Kraft process of wood pulp manufacture.

The distilled tall oils may also be used as an extraction solvent.

The phosphine oxides may be chosen from tri-n-hexylphosphine oxide, tri-n-octylphosphine oxide, tris(2,4,4-trimethylpentyl)phosphine oxide, tricyclohexylphosphine oxide, tri-n-dodecylphosphine oxide, tri-n-octadecylphosphine oxide, tris(2-ethylhexyl)phosphine oxide, di-n-octylethylphosphine oxide, di-n-hexylisobutylphosphine oxide, octyldiisobutylphosphine oxide, tribenzylphosphine oxide, di-n-hexylbenzylphosphine oxide, di-n-octylbenzylphosphine oxide, and any mixture of at least two of them. Tri-n-octylphosphine oxide is preferred. The phosphine oxides may be used alone, in combination or in solution in mixtures of hydrocarbons. Mixtures that are liquid at ambient temperature are preferred.

The liquid/liquid extraction operation is generally carried out at a temperature of at least 10° C., usually at least 15° C., frequently at least 20° C. and more specifically at least 25° C.

This temperature is generally at most 160° C., usually at most 120° C., frequently at most 100° C. and more specifically at most 80° C.

In this third embodiment, the liquid/liquid extraction may be carried out under a pressure of 1 bar absolute, under a pressure above 1 bar absolute or under a pressure below 1 bar absolute. It is preferred to carry out the liquid/liquid extraction operation under a pressure of at most 10 bar absolute, usually at most 5 bar and frequently at most 2 bar. This pressure is generally at least 0.5 bar absolute, usually at least 0.7 bar, frequently at least 0.9 bar and more specifically at least 1 bar.

In the third embodiment of the process according to the invention, recovered at the end of the treatment from step c) is a first cut containing the organic solvent and most of the organic compounds which were contained in the second fraction separated before the treatment from step c), such as epichlorohydrin, light organic compounds, that is to say, organic compounds having boiling points below that of epichlorohydrin, such as acrolein, and heavy organic compounds, that is to say, organic compounds having boiling points between that of epichlorohydrin and of dichloropropanol, such as glycidol and 2-chloro-2-propen-1-ol, super-heavy compounds, that is to say, ones having boiling points above that of dichloropropanol, such as glycerol, 3-chloro-1,2-propanediol, 2-chloro-1,3-propanediol and partially chlorinated and/or esterified polyglycerols.

This first cut may be subjected to one or more supplementary distillation operations in order to separate the solvent from the various organic compounds.

This first cut may be recycled to step a) of the process according to the invention, more particularly when the solvent used for the liquid-liquid extraction is dichloropropanol.

In the third embodiment of the process according to the invention, recovered at the end of the treatment from step c) is a second cut which forms the aqueous composition according to the invention and which contains water, salt, the organic extraction solvent, hydrophilic compounds such as glycerol for instance and a fraction of organic compounds present in the second fraction separated at step b) and which have not been extracted by the organic extraction solvent. The salt content is higher than or equal to 30 g/kg. The total organic carbon content of this second part is less than 5 gC/l, frequently less than 1 g C/l. This second cut comprises at least one carboxylic acid.

In a fourth embodiment of the process for manufacturing the product according to the invention, the treatment from step c) is a physical treatment and comprises a combination of at least two of the operations described in the first three embodiments.

In a first variant of the fourth embodiment, the physical treatment comprises at least one liquid/liquid extraction operation and one stripping operation. These operations may be carried out in any order. It is preferable, however, to carry out the liquid/liquid extraction operation before the stripping operation. The stripping operation may be carried out with steam, air, nitrogen, combustion gases or carbon dioxide, preferably with air or steam.

In this variant, recovered at the end of the liquid/liquid extraction operation is a cut which contains water, salt and organic extraction solvent, and this cut is subjected to a stripping operation. Recovered at the end of the stripping operation is a part which contains water and salt, and of which the total organic carbon content is less than or equal to 2 g C/l, preferably less than 1 g C/l, more preferably less than 0.05 g C/l and even more preferably less than 0.01 g C/l, and this part forms the aqueous composition according to the invention. This part comprises at least one carboxylic acid.

In a second variant of the fourth embodiment, the physical treatment comprises at least one stripping operation and one adsorption operation. These operations may be carried out in any order. It is preferable, however, to carry out the stripping operation before the adsorption operation.

In this variant, recovered at the end of the stripping operation is one part which contains water, salt, epichlorohydrin, dichloropropanol and super-heavy organic compounds, that is to say, ones having boiling points above that of dichloropropanol, and this part is subjected to an adsorption operation. Recovered at the end of the adsorption operation is one part which contains water and salt, and of which the total organic carbon content is less than or equal to 2 g C/l, preferably less than 1 g C/l, more preferably less than 0.05 g C/l and even more preferably less than 0.01 g C/l, and this part forms the aqueous composition according to the invention. This part and comprises at least one carboxylic acid. The salt content is higher than or equal to 30 g/kg.

In a third variant of the fourth embodiment, the physical treatment comprises at least one liquid/liquid extraction operation, one stripping operation and one adsorption operation. These operations may be carried out in any order. It is preferable, however, to carry out the liquid/liquid extraction operation before the stripping operation, and to finish the treatment with the adsorption operation.

In this variant, recovered at the end of the liquid/liquid extraction operation is a cut which contains water, salt and organic extraction solvent, and this cut is subjected to a stripping operation. Recovered at the end of the stripping operation is one part which contains water and salt, and of which the total organic carbon content is less than or equal to 5 g C/l, preferably less than or equal to 4 g C/l, more preferably less than or equal to 2 g C/l, preferably less than 1 g C/l, more preferably less than 0.05 g C/l and even more preferably less than 0.01 g C/l, and this part is subjected to an adsorption operation. Recovered at the end of the adsorption operation is one portion which contains water and salt, and of which the total organic carbon content is less than or equal to 2 g C/l, preferably less than or equal to 1 g C/l, more preferably less than or equal to 0.1 g C/l, yet more preferably less than or equal to 0.01 g C/l, still more preferably less than or equal to 0.005 g C/l, particularly preferably less than 0.001 g C/l and more preferably less than 0.5 mg C/l, and this portion forms the aqueous composition according to the invention. This portion comprises at least one carboxylic acid. The salt content is higher than or equal to 30 g/kg.

In these three variants, the stripping operation is preferably carried out with steam, in a column or by expansion under vacuum (steam generated by the expansion) or by air in an adiabatic column such as described in the third variant of the first embodiment, the extraction operation is preferably carried out with a mixture of 1,3-dichloropropan-2-ol and 2,3-dichloropropan-1-ol, containing at least 50 wt % of 1,3-dichloropropan-2-ol with respect to the sum of the weights of 1,3-dichloropropan-2-ol and 2,3-dichloropropan-1-ol, and the dichloropropanol mixture used is preferably derived from a process for manufacturing dichloropropanol via chlorination of glycerol, and the adsorption operation is preferably carried out with an ion-exchange resin or activated carbon, more preferably with activated carbon.

In a fifth embodiment of the process for manufacturing the product according to the invention, the treatment from step c) is a chemical treatment and comprises at least one oxidation operation. The oxidation operation may be carried out using any oxidizing agent. The oxidizing agent preferably comprises a compound chosen from peroxygenated compounds, such as hydrogen peroxide, inorganic peracids such as perboric acid, inorganic peroxides such as perborates, persulphates and percarbonates, air, oxygen, ozone, chlorinated oxidizing compounds such as molecular chlorine, dichlorine oxide, chlorine dioxide, perchloric, chloric, chlorous and hypochlorous acids and the corresponding salts, perchlorates, chlorates, chlorites and hypochlorites, and mixtures of at least two of them. These oxidizing compounds may be used in combination with activators or catalysts, such as ultraviolet radiation combined with hydrogen peroxide or ozone, and iron salts combined with hydrogen peroxide (Fenton system). The oxidation operation is carried out in a batch reactor or in a continuous reactor, preferably a continuous reactor. The oxidizing agent is introduced into the second fraction before or in the reactor where the main part of the oxidation reaction is carried out. Advantageously, the operation is carried out in a set of reactors in series, the addition of the oxidant being carried out in or before the first reactor or being distributed in or before at least two reactors. Preferably, the oxidizing agent is distributed in or before at least two reactors.

The oxidation operation is preferably carried out using an oxidizing agent that comprises chlorine. The latter may be used in the liquid or gaseous molecular form, in hypochlorous acid form or in hypochlorite form. In gaseous molecular form, it may be used as a mixture with other gases such as air, nitrogen and oxygen for example. The hypochlorous acid and hypochlorite are usually used in the form of aqueous solutions. The total amount of chlorine or of chlorine equivalent used in the oxidation operation is generally at least 7 g of chlorine (expressed as $Cl_2$)/g of total organic carbon (TOC), preferably at least 14 g of chlorine/g of TOC and more preferably at least 17 g of chlorine/g of TOC. The amount of chlorine or of chlorine equivalent used is generally at most 85 g of chlorine/g of TOC, usually at most 55 g of chlorine/g of TOC, preferably at most 40 g of chlorine/g of TOC and most preferably at most 30 g of chlorine/g of TOC. The TOC is the total organic content of the second fraction separated at step b) before the oxidation treatment of step c).

The oxidation operation is carried out at a temperature which is generally at least 10° C., usually at least 30° C., frequently at least 60° C. and more specifically at least 80° C. This temperature is generally at most 200° C., usually at most 180° C., frequently at most 160° C. and more specifically at most 135° C. The oxidation operation may be carried out under a pressure of 1 bar absolute, under a pressure above 1 bar absolute or under a pressure below 1 bar absolute. It is preferred to carry out the oxidation operation under a pressure that is regulated or set between 1 and 11 bar absolute, more preferably under a pressure of 1.1 to 7 bar and most preferably under a pressure of 1.1 to 4 bar.

In a first variant of the fifth embodiment, the oxidation operation is carried out at a pH which is generally at least 7, usually at least 8, often at least 8.5 and frequently at least 9. This pH is generally at most 13, usually at most 12 and frequently at most 11. The pH is generally obtained by addition of a basic compound to the second fraction separated in step b) before addition of chlorine or during the introduction of chlorine. This basic compound may be an organic or inorganic basic compound. Organic basic compounds are for example amines, phosphines or arsines, preferably sterically hindered, and ammonium, phosphonium or arsonium hydroxides. Inorganic basic compounds are preferred. The expression "inorganic compounds" is understood to mean compounds which do not contain a carbon-hydrogen bond.

The inorganic basic compound may be chosen from alkali and alkaline-earth metal oxides, hydroxides, carbonates, hydrogen carbonates, phosphates, hydrogen phosphates and borates, and mixtures thereof. Alkali and alkaline-earth metal oxides and hydroxides are preferred. Alkali metal hydroxides are more preferred and sodium hydroxide is particularly preferred.

The basic agent may be in the form of a liquid, an essentially anhydrous solid, a hydrated solid, an aqueous and/or organic solution or an aqueous and/or organic suspension. The basic compound is preferably in the form of an essentially anhydrous solid, a hydrated solid, an aqueous solution or an aqueous suspension.

The preferred basic compounds are in the form of concentrated aqueous solutions or suspensions of sodium hydroxide or calcium hydroxide or in the form of purified caustic brine, preferably in the form of concentrated aqueous solutions or suspensions of sodium hydroxide, or the form of purified caustic brine. The expression "purified caustic brine" here means sodium hydroxide which contains sodium chloride such as, for example, that produced in a membrane electrolysis process.

The reaction time in a batch reactor, or the total residence time in a continuous reaction zone, is generally from 0.1 to 8 h, preferably from 0.25 to 8 h, particularly preferably from 0.5 to 6 h and more preferably from 1 to 4 h.

At the end of the oxidation operation, the second fraction separated in step b) contains water, salt, residual oxidizing agent, oxidation products such as carbonates, hydrogen carbonates, carboxylic acids including formic acid, traces of aldehydes, and has a total organic carbon content that is often less than or equal to 2 g C/l, preferably less than or equal to 1 g C/l, more preferably less than or equal to 0.1 g C/l, still more preferably less than or equal to 0.05 g C/l, yet more preferably less than or equal to 0.01 g C/l, particularly more preferably less than or equal to 0.005 g C/l, still particularly more preferably less than or equal to 0.005 g C/l, and yet more preferably less than or equal to 0.002 g C/l, most preferably less than or equal to 0.001 g C/l and particularly most preferably less than or equal to 0.5 mg C/l and this treated fraction forms the aqueous composition according to the invention. The salt content is higher than or equal to 30 g/kg.

In a second variant of the fifth embodiment, the second fraction separated in step b) is reacted in a liquid reaction medium, in a first stage (i) with at least one composition comprising hydroxide ions ($OH^-$) and hypochlorite in a molar ratio between hydroxide and hypochlorite higher than or equal to 0.001 and lower than 1.5.

In stage (i), the composition containing the hypochlorite can be a solid, an aqueous solution containing hypochlorous acid and sodium hypochlorite.

In this second variant, the reaction of stage (i) can be carried out at a pH higher than or equal to 6 and lower than or equal to 11, preferably higher than or equal to 7 and lower than or equal to 10 and most preferably higher than or equal to 7.5 and lower than or equal to 9. The pH has generally to be maintained at such set values since pH changes occur during the course of the oxidation reaction. The pH can be maintained at said values either by addition of an acidic compound or by addition of a basic compound. Any acidic or basic compounds can be used to maintain the pH. Inorganic acids and inorganic bases are preferred. Hydrogen chloride, gaseous and/or in aqueous solution, is a more preferred acidic compound. Sodium or calcium hydroxides, solids and/or in aqueous solution and/or suspensions, are more preferred basic compounds, with sodium hydroxide aqueous solutions being most preferred.

In this second variant, the reaction of stage (i) can be carried out at a temperature higher than or equal to 30° C. and lower than or equal to 180° C., more preferably higher than or equal to 60° C. and lower than or equal to 160° C., and most preferably higher than or equal to 80° C. and lower than or equal to 135° C.

In this second variant, the reaction of stage (i) can be carried out at a pressure higher than or equal to 0.9 bar (absolute) and lower than or equal to 11 bar, preferably higher than or equal to 1 bar (absolute) and lower than or equal to 7 bar, and most higher than or equal to 1.1 bar (absolute) and lower than or equal to 4 bar.

In this second variant, the first stage (i) can be operated in a batch mode, a continuous mode or a semi-continuous mode.

In this second variant, the reaction of stage (i) when stage (i) is operated under batch mode can be carried out for a duration higher than or equal to 0.1 h and lower than or equal to 8 h, preferably higher than or equal to 0.25 h and lower than or equal to 3 h, and most preferably higher than or equal to 0.5 h and lower than or equal to 2 h.

In this second variant, the reaction of stage (i) when stage (i) is operated under continuous mode can be carried out for a total residence time in the continuous reaction zone higher than or equal to 0.1 h and lower than or equal to 8 h, preferably higher than or equal to 0.25 h and lower than or equal to 3 h, and most preferably higher than or equal to 0.5 h and lower than or equal to 2 h.

In the process according to the invention, the reaction of step (i) can be carried out in one or more reaction zones, preferably at least two reaction zones and more preferably at least three reaction zones. The reactions zones may be composed of volumes assembled in a single jacket or volumes in separate jackets. In the case where the volumes are assembled in a single jacket, the reaction zones may be positioned horizontally or vertically with respect to one another. In any case, the transfer from one zone to another may take place by gravity or by forced circulation. These reaction zones may be placed in any configuration, in series, in parallel or some in series and others in parallel. These reactions zones can be operated under any type of regime, like for instance perfectly mixed regime or plug flow regime. It is preferred that at least one of the zone is operated under perfectly mixed regime and at least another one is operated under plug flow regime, and it is more preferred that the zone operating under plug flow regime is located after the zone operating under perfectly mixed regime. Such conditions are especially well suited when the process is carried out under continuous mode.

In the process according to the invention, the reaction zones may be supplied independently of one another, with the second fraction separated in step b) to be treated, with the composition containing the hypochlorite, with any other compositions, or with at least two of these compositions. The other composition may comprise for instance the acidic or the basic compound used to adjust the pH of the liquid reaction medium, or a stripping gas to remove volatile reactions products. When several reaction zones are in series, it is preferred to supply the major part of the aqueous composition containing the hypochlorite in the first reaction zone of the series. The pH of the liquid reaction medium is preferably adjusted independently in the different reaction zones of the series.

That first stage (i) can be followed by a second stage (ii) where, at least one part of the reaction medium of the first stage (i) is subjected to an acidification operation in order to bring the pH at a second value which is lower than the pH value of the first stage (i), and the organic substances are further oxidized. The pH can be maintained at said values either by addition of an acidic compound or by addition of a basic compound. Such compounds are as described in the second variant of the fifth embodiment.

The reaction conditions are as described in the European Patent Application EP 08150925.9 filed on 31 Jan. 2008 in the name of SOLVAY SA and entitled "Process for degrading organic contaminants in an aqueous composition", the content of which is hereby incorporated by reference.

Figure 1:
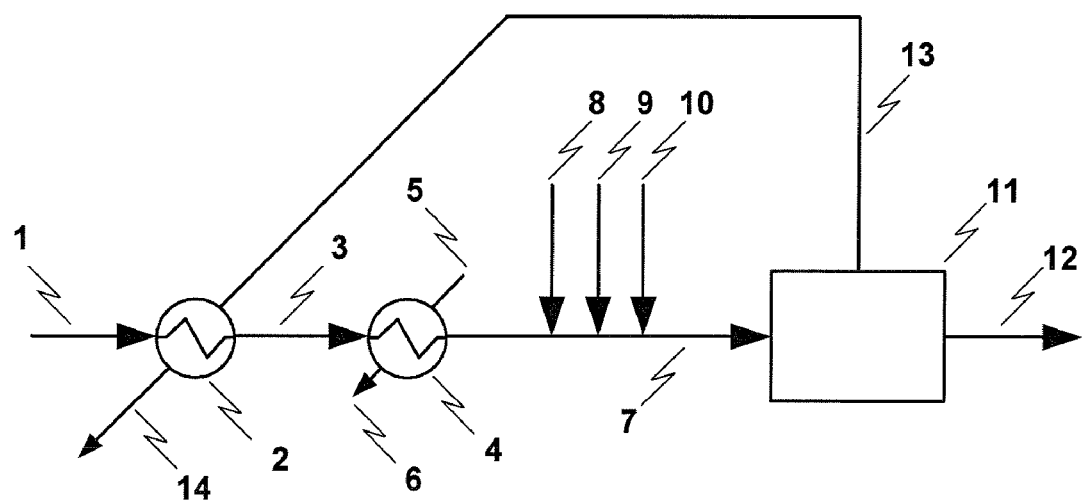
FIG. 1: Flow-sheet of the process according to the fifth embodiment of the invention.

A way of conductive the fifth embodiment is presented in FIG. 1.

An aqueous composition containing sodium chloride and organic compounds is supplied through line (1) to a first heat exchanger (2) at a flow rate of 40 m$^3$/h where it is heated up, then through line (3) to a second heat exchanger (4) where it is further heated up and then through line (7) to a series of three reactors (11). Steam is introduced in the second heat-exchanger (4) through line (5) and withdrawn through line (6). Sodium hydroxide, hydrogen chloride and hypochlorite are introduced respectively through lines (8), (9) and (10) to the flow of line (7). Sodium hydroxide and hydrogen chloride are used for pH adjustment, and hypochlorite for destruction of the organics present in stream (7). A gaseous effluent which comprises chlorine and carbon dioxide the contents of which depend on the pH conditions chosen for the oxidation reaction is withdrawn for the series of reactors (11) through line (12) and send to the manufacture of vinyl chloride monomer. A liquid effluent is withdrawn from the series of reactors (11) through line (13) and is used to heat up in the first heat exchanger (2) through line (13) and is further fed to a electrolysis unit through line (14) at a flow rate of 40 m$^3$/h. The series of reactors is operated at 130° C. and the total residence time is about 1.5 hour.

In a sixth embodiment of the process for manufacturing the product according to the invention, the treatment from step c) comprises at least one physical treatment chosen from the physical treatments described in embodiments 1 to 3, and a chemical treatment such as described in the fifth embodiment. It is preferred to carry out the stripping operation with steam. It is more preferable to carry out the oxidation operation in the presence of an oxidizing agent containing active chlorine.

In a first variant of the sixth embodiment, the treatment comprises at least one stripping operation and one oxidation operation. These operations may be carried out in any order. It is preferable, however, to carry out the stripping operation before the oxidation operation.

Recovered at the end of the stripping operation is one part which contains water, salt, epichlorohydrin, dichloropropanol and super-heavy organic compounds, that is to say, compounds having boiling points above that of dichloropropanol, and of which the total organic carbon content is generally less than 5 g C/l, preferably less than or equal to 4 g C/l, more preferably less than or equal to 2 g C/l, still more preferably less than 1 g C/l, yet more preferably less than 0.1 g C/l and most preferably less than 0.01 g C/l, and this part is subjected to an oxidation operation. At the end of the oxidation operation, the treated part contains water, salt, residual oxidizing agent, oxidation products such as carbonates, hydrogencarbonates, carboxylic acids, salts of carboxylic acids, including formic acid or salts of formic acid, traces of aldehydes, and has a total organic carbon content that is usually less than or equal to 2 g C/l, preferably less than or equal to 1 g C/l, more preferably preferably less than or equal to 0.1 g C/l, yet more preferably less than or equal to 0.05 g C/l, still more preferably less than 0.01 g C/l, particularly more preferably less than or equal to 0.005 g C/l, yet particularly more preferably less than or equal to 0.002 g C/l, most preferably less than or equal to 0.001 g C/l and particularly most preferably less than or equal to 0.5 mg C/l, and this treated part forms the aqueous composition according to the invention. The salt content is higher than or equal to 30 g/kg.

In a second variant of the sixth embodiment, the treatment comprises at least one liquid/liquid extraction operation, one stripping operation and one oxidation operation. These operations may be carried out in any order. It is preferable, however, to carry out the liquid/liquid extraction operation before the stripping operation, and to finish the treatment with the oxidation operation.

Recovered at the end of the liquid/liquid extraction operation is a cut which contains water, salt and organic extraction solvent, and this cut is subjected to the stripping operation. Recovered at the end of the stripping operation is one part which contains water and salt, and of which the total organic carbon content is at most 5 g C/l, preferably at most 2 g C/l, preferably less than or equal to 1 g C/l, more preferably less than or equal to 0.1 g C/l, yet more preferably less than or equal to 0.05 g C/l and most preferably less than 0.01 g C/l, and this part is subjected to an oxidation operation. At the end of the oxidation operation, the treated part contains water, salt, residual oxidizing agent, oxidation products such as carbonates, hydrogen carbonates, carboxylic acids including formic acid, traces of aldehydes, and has a total organic carbon content that is usually less than or equal to 2 g C/l, preferably less than or equal to 1 g C/l, more preferably preferably less than or equal to 0.1 g C/l, yet more preferably less than or equal to 0.05 g C/l, still more preferably less than 0.01 g C/l, particularly more preferably less than or equal to 0.005 g C/l, yet particularly more preferably less than or equal to 0.002 g C/l, most preferably less than or equal to 0.001 g CA and particularly most preferably less than or equal to 0.5 mg C/l, and this treated part forms the aqueous composition according to the invention. The salt content is higher than or equal to 30 g/kg.

In these two variants of the sixth embodiment, the stripping operation is preferably carried out with steam and under the conditions described in the third variant of the first embodiment, the oxidation operation is preferably carried out with an oxidizing agent mainly composed of active chlorine, under the conditions described in the first and second variant of the fifth embodiment. When a basic agent or an acidic agent is used to adjust and or control the pH, it is generally introduced after the last physical treatment and before the chemical treatment, and/or during the chemical treatment. The extraction operation is preferably carried out with a mixture of 1,3-dichloropropan-2-ol and 2,3-dichloropropan-1-ol, containing at least 50 wt % of 1,3-dichloropropan-2-ol, and the dichloropropanol mixture used is preferably derived from a process for manufacturing dichloropropanol via chlorination of glycerol.

After the chemical treatment, it can be useful to eliminate the excess of oxidant, e.g active chlorine, used to carry out the oxidation reaction. This can be carried out by adding some reducing species to the medium at the end of the oxidation treatment, like for instance hydrogen peroxide, sulfite or bisulfite. An alternative is the acidification of the medium at the end of the oxidation treatment in combination with an operation of evaporation or stripping at an adequate temperature and possibly under a slight vacuum. Under such conditions excess active chlorine for instance will be converted to molecular chlorine and stripped out of the medium. The excess of active chlorine can then be recycled to the chemical oxidation treatment as such or under the hypochlorite form after dissolution in a base solution.

In a third and a fourth variant of the sixth embodiment, the procedure of the first variant or of the second variant respectively of the sixth embodiment is followed and the treated part is subjected, at the end of the oxidation operation, to a chemical operation of catalytic reduction via hydrogen in the presence of a catalyst based on a supported noble metal as described in Applications WO 98/37024 in the name of Solvay Deutschland GmbH and WO 96/07617 in the name of Solvay Umweltchemie GmbH.

In the process for manufacturing the aqueous composition according to the invention (brine according to the invention for short), steps a) to c) are preferably carried out in equipment produced from or covered with materials that are resistant to the basic compound under the step a) reaction conditions, step b) settling conditions and step c) treatment conditions, and resistant to the oxidizing agent under the step c) treatment conditions.

The materials that are resistant to the basic compound may be chosen from metals such as carbon steel, stainless steel and nickel, coated metals such a glass-lined steel and from plastics such as polytetrafluoroethylene and polypropylene.

The materials that are resistant to the oxidizing agent are preferably chosen from metals such as titanium, metal alloys such as Hastelloy C, and enameled steel.

In the process for manufacturing the aqueous composition according to the invention, others steps than a), b) and c) are generally carried out in equipment produced from or covered with materials which do not release metal ions in the brine of the invention under the operating conditions of those steps. Such other steps are for instance, steps of storage, supply, withdrawal, transfer, chemical treatment or physical treatment of compounds used or produced in the process for preparing the brine of the invention. Examples of these steps have been described above.

Among the steps of storage mention may be made, for example, of the storage of the basic agent, of the dichloropropanol, and of the aqueous composition of the invention. Among the steps of physical treatment mention may be made, for example, of the operations of separation by stripping, distillation, evaporation, extraction, decantation and filtration and of the operations of heat exchange, heating and cooling.

Among the steps of supply, withdrawal or transfer mention may be made, for example, of the operations of recycling, the transport of fluids between the various pieces of apparatus in which the chemical reactions, the storage and the chemical and physical treatments are carried out.

"Apparatus" refers to for instance containers in which compounds are stored, chemical reactions are carried out and/or physical operations are carried out, the pipes and connectors connecting these containers, elements ensuring leaktight connections, instruments necessary for the transfer of compounds between the containers, instruments and equipment for measuring the various parameters necessary for the monitoring of the storage, for the transfer of the compounds and for the carrying-out of the chemical reactions and the physical operations.

By way of suitable material, mention may be made, for example, of enameled steel, polymers like, polyolefins such as polypropylene and polyethylene, fluorinated polymers such as polytetrafluoroethylene, poly(vinylidene fluoride) and poly(perfluoropropylvinylether), polymers comprising sulphur, such as polysulphones or polysulphides, in particular aromatic, coatings by means of resins among which, epoxy resins or phenolic resins, metals or alloys thereof, in particular tantalum, titanium, copper, gold and silver, nickel and molybdenum, more particularly alloys containing nickel and molybdenum, ceramics, metalloceramics, refractory materials, and graphite, which may or may not be impregnated.

The invention also relates to the use of the aqueous composition according to the invention as a reactant in an electrolysis process, preferably in an electrolysis process intended for the production of chlorine, sodium hydroxide and hydrogen, more particularly preferably in an electrolysis process intended for the production of chlorine.

In the use of the aqueous composition according to the invention, a fraction of the sodium hydroxide resulting from the electrolysis process may be recycled to step a) to react with dichloropropanol in order to obtain epichlorohydrin and an aqueous composition containing sodium chloride. The aqueous composition containing sodium chloride may be reacted with active chlorine in order to obtain the aqueous composition according to the invention. The active chlorine may contain a fraction of the chlorine produced by the electrolysis process.

In the use of the aqueous composition according to the invention, a fraction of the chlorine resulting from the electrolysis process may be reacted with hydrogen and/or with a compound selected from propylene, methane, a chlorinated hydrocarbon, a chlorohydrofluorocarbon, or a mixture thereof, in order to obtain hydrogen chloride. A fraction of the hydrogen may be obtained in the electrolysis process.

In the use of the aqueous composition according to the invention, a fraction of the chlorine resulting from the electrolysis process may be reacted with silicon, with high silicon ferro-silicon, with silicon carbide, with silica in the presence of carbon, in order to obtain silicon tetrachloride and/or with ethylene in order to obtain 1,2-dichloroethane and/or carbon monoxide in order to obtain phosgene. The silicon tetrachloride may be further submitted to flame hydrolysis, the 1,2-dichloroethane may be further submitted to pyrolysis and the phosgene may be further reacted with amines in order to obtain hydrogen chloride. A fraction of the obtained hydrogen chloride may be further reacted with glycerol in order to obtain dichloropropanol. A fraction of the dichloropropanol may reacted with sodium hydroxide in order to obtain epichlorohydrin and an aqueous composition containing sodium chloride.

A fraction of the chlorine resulting from the electrolysis process may also be recycled in the chemical treatment used for preparing the brine according to the invention.

The electrolysis process may be a mercury electrolysis, a diaphragm electrolysis or a membrane electrolysis process. These processes are described in Ullmann's Encyclopedia of Industrial Chemistry, Fifth Completely Revised Edition, Vol. A6 1986, pp. 401-477). The electrolysis process is preferably a membrane electrolysis process.

The various electrolysis processes generally comprise several steps, in addition to the electrolysis step itself, like for instance brine saturation, brine purification by for instance precipitation, filtration, fine purification (ion-exchange), brine pH adjustment, before the electrolysis and brine dechlorination, chlorate, bromate and iodate destruction, and pH adjustment, in the brine recycling loop. Those steps are represented in "Ullmann's Encyclopedia of Industrial Chemistry, Fifth, Completely Revised Edition, Volume A6, 1986, page 407, FIGS. 9, 10 and 11".

Figure 2:
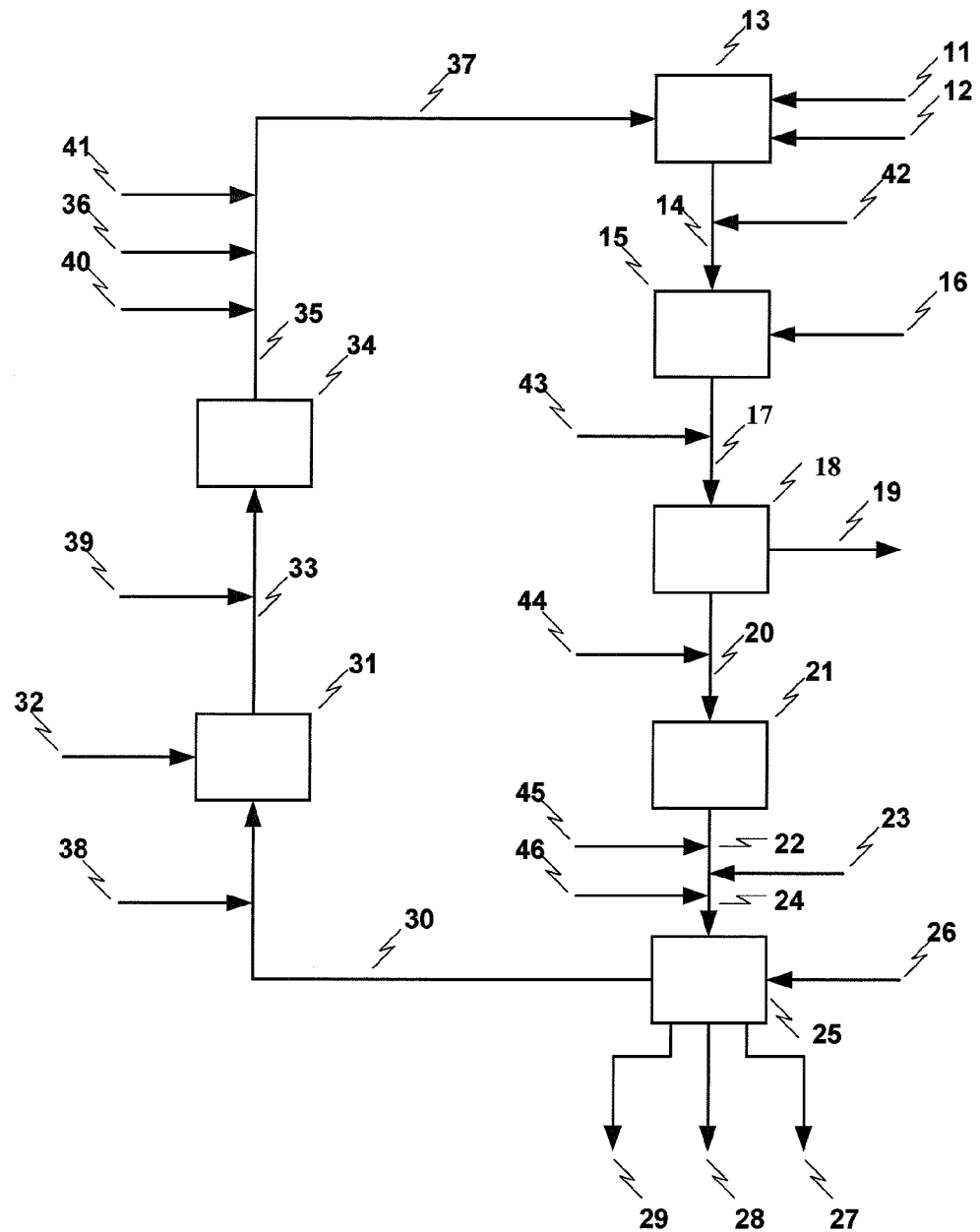
FIG. 2: Flow-sheet of a membrane chlorine electrolysis process.

FIG. 2 represents a flow-sheet of a first electrolysis process, which is typical of a membrane chlorine electrolysis process.

Water and salt are added through lines (11) and (12) to a brine saturation unit (13). A stream of raw brine is withdrawn from the brine saturation unit (13) through line (14) and is fed to a precipitation unit (15). Precipitation agents are added to the precipitation unit (15) through line (16). A stream is withdrawn from the precipitation unit (15) through line (17) and is fed to a filtration unit (18). A stream which constitutes the residue of the filtration unit is withdrawn from the filtration unit (18) through line (19). Another stream is withdrawn from the filtration unit (18) through line (20) and is fed to a fine purification unit (21). A stream of purified brine is withdrawn from the fine purification unit (21) through line (22). A stream of hydrochloric acid can possibly be added to stream (22) through line (23) and the resulting stream is fed to an electrolysis unit (25) through line (24). The electrolysis unit is also fed by a stream of caustic solution through line (26). A stream of caustic solution is withdrawn from the electrolysis unit (25) through line (27). A fraction of that stream can be recycled to line (8) of FIG. 1. A stream of chlorine is withdrawn from the electrolysis unit (25) through line (28). A fraction of that stream can be recycled to line (9) of FIG. 1. A stream of hydrogen is withdrawn from the electrolysis unit (25) through line (29). Both streams from lines (28) and (29) can be fed to a unit for producing hydrogen chloride. A stream of depleted brine is withdrawn from the electrolysis unit (25) through line (30) and is fed to a chlorate destruction unit (31). The chlorate destruction unit is also fed with a stream of hydrochloric acid through line (32). The chlorate destruction unit may optionally be a catalytic chlorate reduction unit containing a noble metal supported catalyst. The chlorate destruction unit is in this case fed with a stream of hydrogen through line (32). A stream is withdrawn from the chlorate destruction unit (31) through line (33) and is fed to a dechlorination unit (34). A stream is withdrawn from the dechlorination unit (34) through line (35). A stream of caustic solution is added to stream (35) through line (36) and the resulting stream is fed to the brine saturation unit (13) through line (37).

With reference to FIG. 2, the aqueous composition according to the invention can be added at any stage for example through line (38) and/or line (39) and/or (40) and/or (41) and/or (42) and/or (43) and/or (44) and/or (45) and/or (46).

Figure 3:
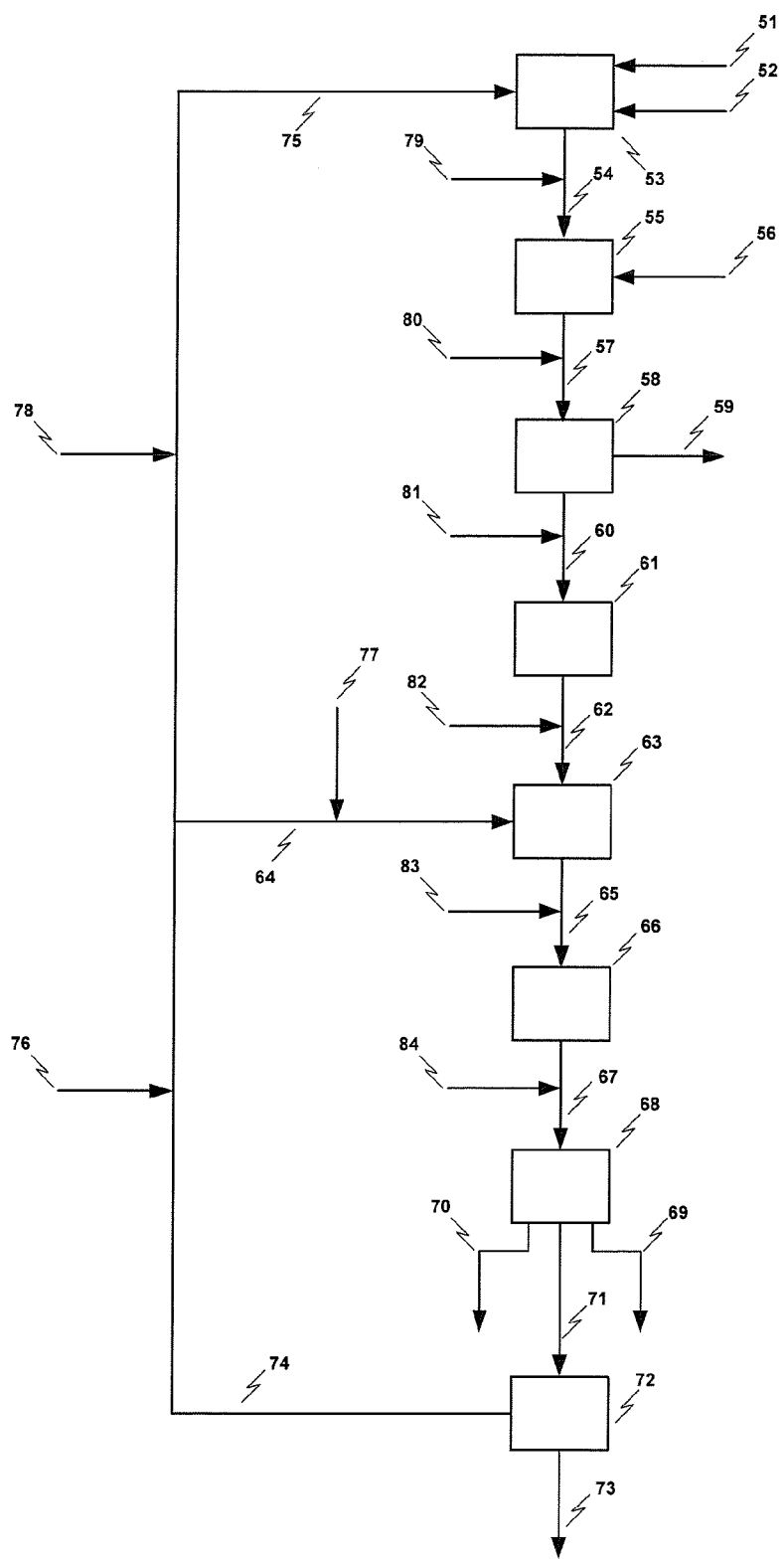
FIG. 3: Flow-sheet of a diaphragm chlorine electrolysis process.

FIG. 3 represents a flow-sheet of a second electrolysis process which is typical of a diaphragm chlorine electrolysis process. Water and salt (brine) are added though lines (51) and (52) to a first brine saturation unit (53). A stream of raw brine is withdrawn from the first brine saturation unit (53) through line (54) and is fed to a precipitation unit (55). Precipitation agents are added to the precipitation unit (55) through line (56). A stream is withdrawn from the precipitation unit (55) through line (57) and is fed to a filtration unit (58). A stream which constitute the residue of the filtration unit is withdrawn from the filtration unit (58) through line (59). Another stream is withdrawn from the filtration unit (58) through line (60) and is fed to a first heat exchange unit (61). A stream is withdrawn from the first heat exchange unit (61) through line (62) and fed to a second brine saturation unit (63) and the second brine saturation unit is fed with a stream of salt through line (64). A stream is withdrawn from the second brine saturation unit (63) through line (65) and is fed to a second heat exchange unit (66). A stream is withdrawn from the second heat exchange unit (66) through line (67) and fed to an electrolysis unit (68). A stream of hydrogen is withdrawn from the electrolysis unit (68) through line (69). A stream of chlorine is withdrawn from the electrolysis unit (68) through line (70). A fraction of that stream (70) can be recycled to line (9) of FIG. 1. Both streams from lines (69) and (70) can be fed to a unit for producing hydrogen chloride. A stream is withdrawn from the electrolysis unit (68) through line (71) and fed to a concentration unit (72). A stream of caustic solution is withdrawn from the concentration unit (72) through line (73). A fraction of that stream can be recycled to line (8) of FIG. 1. A stream of depleted brine is withdrawn from the concentration unit (72) through line (74) and is fed through line (64) to the second brine saturation unit (63) and through line (75) to the first brine saturation unit (53).

With reference to FIG. 3, the aqueous composition according to the invention can be added at any stage for example through line (76) and/or line (77) and/or (78) and/or (79) and/or (80) and/or (81) and/or (82) and/or (83) and/or (84).

Figure 4:
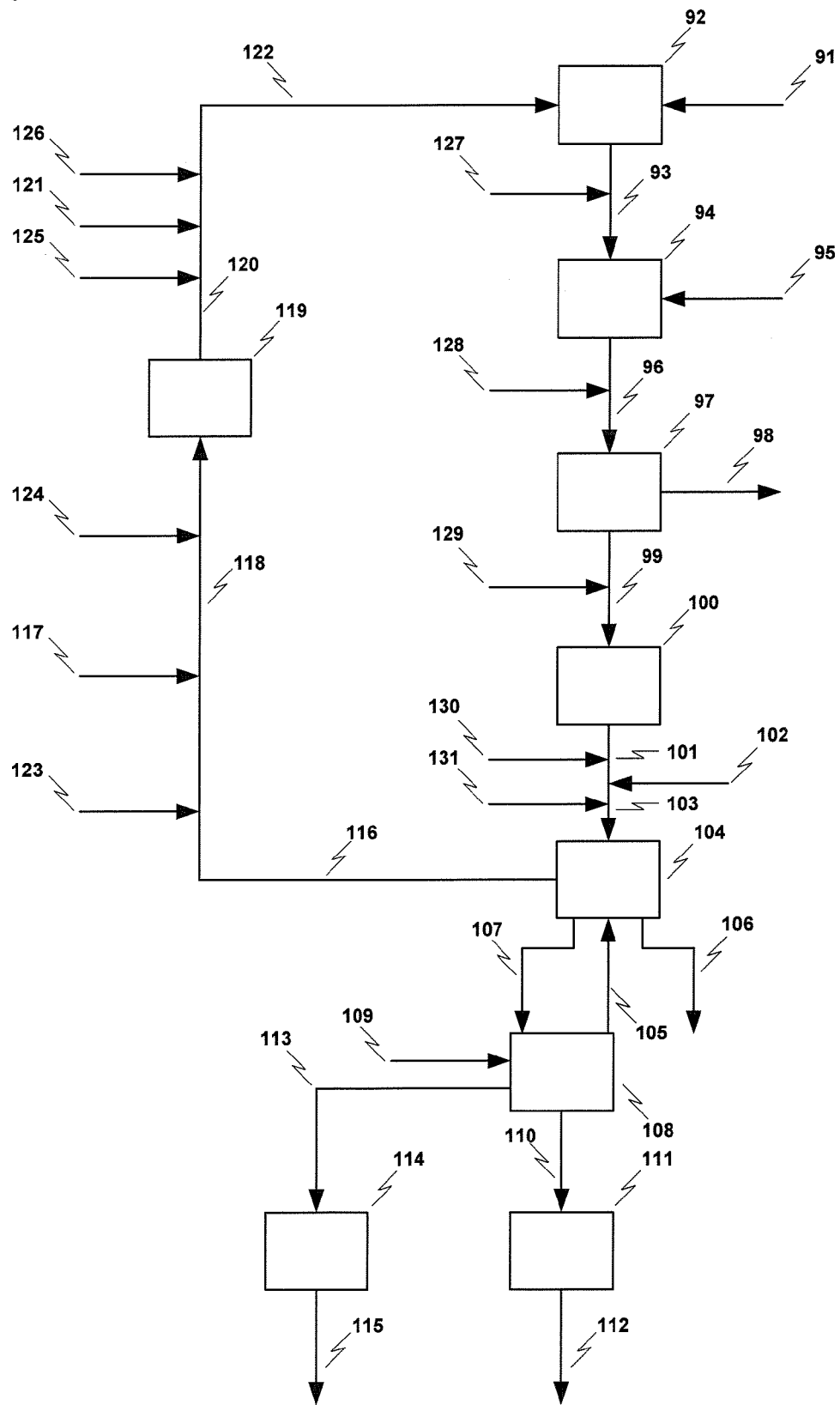
FIG. 4: Flow-sheet of a mercury chlorine electrolysis process.

FIG. 4 represents a flow-sheet of a third electrolysis process which is typical of a mercury chlorine electrolysis process. Salt is added through line (91) to a brine saturation unit (92). A stream of raw brine is withdrawn from the brine saturation unit (92) through line (93) and is fed to a precipitation unit (94). Precipitation agents are added to the precipitation unit (94) through line (95). A stream is withdrawn from the precipitation unit (94) through line (96) and is fed to a filtration unit (97). A stream which constitutes the residue of the filtration unit is withdrawn from the filtration unit (97) through line (98). Another stream is withdrawn from the filtration unit (97) through line (99) and is fed to a cooling unit (100). A stream is withdrawn from the cooling unit (100) through line (101). A stream of hydrochloric acid is fed through line (102) to stream (101). The resulting stream is fed through line (103) to an electrolysis unit (104). The electrolysis unit (104) is fed with mercury through line (105). A stream of chlorine is withdrawn from the electrolysis unit (104) through line (106). A fraction of that stream can be recycled to line (9) of FIG. 1. A stream of amalgam is withdrawn from the electrolysis unit (104) through line (107) and is fed to an amalgam decomposition unit (108). Water is fed through line (109) to the amalgam decomposition unit (108). A stream of hydrogen is withdrawn from the amalgam decomposition unit (108) through line (110) and fed to a first mercury removal unit (111). A stream of hydrogen is withdrawn from the first mercury removal unit (111) through line (112). Both streams from lines (106) and (112) can be fed to a unit for producing hydrogen chloride. A stream of caustic solution is withdrawn from the amalgam decomposition unit (108) through line (113) and fed to a second mercury removal unit (114). A stream of caustic solution is withdrawn from the second mercury removal unit (114) through line (115). A fraction of that stream can be recycled to line (8) of FIG. 1. A stream is withdrawn from the electrolysis unit (104) through line (116). A stream of hydrochloric acid is fed to stream (116) through line (117). The resulting stream is fed to a dechlorination unit (119) through line (118). A stream is withdrawn from the dechlorination unit (119) through line (120). A caustic solution is added to stream (120) through line (121). The resulting stream is fed to the brine saturation unit (92) through line (122).

With reference to FIG. 4, the aqueous composition according to the invention can be added at any stage for example through line (123) and/or line (124) and/or (125) and/or (126) and/or (127) and/or (128) and/or (129) and/or (130) and/or (131).

The aqueous composition according to the invention is preferably added in the recycled brine just after the electrolysis step.

The aqueous composition according to the invention is preferably added in the recycled brine of a membrane electrolysis process just after the electrolysis step. In a membrane electrolysis process, the aqueous composition according to the invention is preferably added after the hydrochloric acid addition and before the electrolysis unit (line (45) of FIG. 2) and/or after the electrolysis unit and before the chlorate destruction unit (line (38) of FIG. 2), and/or after the chlorate destruction unit and before the dechlorination unit (line (39) of FIG. 2). This way of proceeding has the advantage that the excess of active chlorine present in the aqueous composition according to the invention does not need to be eliminated since it will be recovered in the electrolysis dechlorination step.

The electrolysis process comprising the use of the aqueous composition according to the invention as a reactant generally comprises passing a direct current through the aqueous composition or imposing a direct voltage across the aqueous composition. The process preferably comprises passing a direct current through the aqueous composition to be electrolyzed.

In the electrolysis process, the temperature of electrolysis is often lower than or equal to 120° C., frequently lower than or equal to 100° C. and particularly lower than or equal to 90° C. That temperature is usually higher than or equal to 0° C., often higher than or equal to 25° C., frequently higher than or equal to 50° C., particularly higher than or equal to 75° C. and specifically higher than or equal to 80° C. A temperature of 85° C. is particularly convenient.

In the electrolysis process according to the invention, the pressure of electrolysis is often lower than or equal to 5 bar absolute, frequently lower than or equal to 2 bar, particularly lower than or equal to 1.8 bar and specifically lower than or equal to 1.5 bar. That pressure is usually higher than or equal to 0.01 bar absolute, often higher than or equal to 0.1 bar, frequently higher than or equal to 0.5 bar, particularly higher than or equal to 0.6 bar and specifically higher than or equal to 0.7 bar.

The electrolysis process can be carried out continuously or discontinuously. It is often carried out continuously. By continuous process, it is meant that the brine is continuously fed to the zone where the electrolysis occurs (electrolysis zone) and the product resulting from the electrolysis are continuously removed from that zone.

In the electrolysis process, when the electrolysis process is carried out in the batch mode, the reaction time is often lower than or equal to 5 h, frequently lower than or equal to 2 h, particularly lower than or equal to 1 h and specifically lower than or equal to 0.5 h. That time is usually higher than or equal to 0.005 h, often higher than or equal to 0.05 h, frequently higher than or equal to 0.1 h, particularly higher than or equal to 0.15 h and specifically higher than or equal to 0.2 h.

In the electrolysis process, when the electrolysis process is carried out in the continuous mode, the residence time is often lower than or equal to 5 h, frequently lower than or equal to 2 h, particularly lower than or equal to 1 h and specifically lower than or equal to 0.5 h. That residence time is usually higher than or equal to 0.005 h, often higher than or equal to 0.5 h, frequently higher than or equal to 0.1 h, particularly higher than or equal to 0.15 h and specifically higher than or equal to 0.2 h. The residence time is defined as the ratio between the volume of the zone where the electrolysis occurs and the flow rate of the aqueous composition to be electrolyzed to the electrolysis zone.

In the electrolysis process, when the electrolysis is carried out under the direct current mode, the current density passed across the cell is generally higher than or equal to 1 A/m$^2$ of electrode, often higher than or equal to 100 A/m$^2$, frequently higher than or equal to 1000 A/m$^2$ and specifically higher than or equal to 5000 A/m$^2$. That current density is generally lower than or equal to 25000 A/m$^2$ of electrode, often lower than or equal to 20000 A/m², frequently lower than or equal to 15000 A/m² and specifically lower than or equal to 10000 A/m².

In the electrolysis process, when the electrolysis is carried out under the direct voltage mode, the voltage applied between the anode and the cathode is generally higher than or equal to 2.3 V, often higher than or equal to 2.4 V and frequently higher than or equal to 2.5 V. That voltage is generally lower than or equal to 6 V, often lower than or equal to 5 V and frequently lower than or equal to 4 V.

The electrolysis process comprising the use of the aqueous composition according to the invention as a reactant is usually carried out in an electrolysis cell (or unit) comprising at least one anode and at least one cathode.

The electrolysis cell generally comprises the electrolysis zone. The electrolysis zone is usually defined by the part of the cell comprised between the electrodes.

The process of electrolysis generally comprises imposing a direct current or imposing a direct voltage between the cathode and the anode, often comprises imposing a direct current between the cathode and the anode.

In the process of electrolysis, the electrolysis cell can be fed continuously or discontinuously. The feeding of the electrolysis cell is often carried out continuously.

In the process of electrolysis, the products resulting from the electrolysis can be removed from the electrolysis cell continuously or discontinuously. The products are often removed continuously.

The electrolysis cell can be a mercury cell, a diaphragm cell or a membrane cell. It is often a diaphragm cell or a membrane cell, and frequently a membrane cell. A mercury cell is also convenient.

When the electrolysis cell is a diaphragm or a membrane cell, it generally comprises an anolyte chamber containing at least one anode and a catholyte chamber containing at least one cathode, the chambers being separated by a least one diaphragm or at least one membrane. The aqueous composition to be electrolyzed can be fed to the anolyte chamber, to the catholyte chamber or to both chambers of the electrolysis cell. It is often fed to the anolyte chamber.

The characteristics of the various type of electrolysis cells, of the anodes and cathodes, of the membranes and diaphragms, etc. can be found in Ullmann's Encyclopedia of Industrial Chemistry, Fifth Completely Revised Edition, Vol. A6 1986, pp. 401-477.

The present invention relates also to a process for the production of epichlorohydrin comprising:
I. a step of manufacturing dichloropropanol by chlorination of glycerol with hydrogen chloride
II. a step of dehydrochlorination of the dichloropropanol obtained in step (I) with sodium hydroxide in order to obtain epichlorohydrin and an aqueous composition containing sodium chloride
III. a step of treating the aqueous composition of step (II) comprising a reaction with active chlorine in order to obtain an aqueous composition according to the invention
IV. a step of electrolysing the aqueous composition of step (III) in order to obtain hydrogen, chlorine and sodium hydroxide,
and optionally at least one of the following steps
V. a step of recycling in step (II) a fraction of the sodium hydroxide obtained in step (IV)
VI. a step of reacting a fraction of chlorine obtained in step (IV) with
  a. hydrogen obtained in step (IV) and/or
  b. a compound selected from propylene, methane, a chlorinated hydrocarbon, a chlorohydrofluorocarbon, or a mixture thereof
in order to produce hydrogen chloride and recycling a fraction of hydrogen chloride produced in step (VI) in step (I)
VII. a step of reacting a fraction of chlorine obtained in step (IV) with
  a. silicon, high silicon ferro silicon, silicon carbide, silica and carbon, to generate silicon tetrachloride and/or with ethylene to generate 1,2-dichloroethane and/or with carbon monoxide to generate phosgene and/or
  b. submitting silicon tetrachloride and/or 1,2-dichloroethane and/or phosgene to respectively flame hydrolysis, pyrolysis and reaction with amines
in order to produce hydrogen chloride and recycling a fraction of hydrogen produced in step (VII) in step (I)
VIII. a step of recycling a fraction of chlorine obtained in step (IV) in step (III).

The aqueous composition according to the invention may also be involved in a biological treatment or be rejected in a purge. In this case, a supplementary dilution operation is generally required in order to reduce the salt content of said brine.

The examples below are intended to illustrate the invention without, however, limiting it.

EXAMPLE 1

A 1-litre glass thermostated reactor was charged with 258.76 g of 1,3-dichloropropan-2-ol (2.01 mol). Added to the flask over 20 min, at 25° C. and with vigorous stirring, were 397.1 g of a 19.1 wt % aqueous solution of NaOH (1.90 mol). At the end of the addition, the resulting mixture was transferred into a separating funnel. Recovered were 179.39 g of an organic fraction, the density of which was 1.185, and 488.95 g of a second fraction, the density of which was 1.182, the total organic carbon content (TOC) of which was 8.7 g of C/l. An aliquot part of the second fraction was subjected to an evaporation operation under a vacuum of 150 ton at 90° C. until 14.6 wt % of a condensed evaporate and of an evaporation residue, of which the TOC was 0.69 g C/l and of which the main organic constituent was 3-chloro-1,2-propanediol, were recovered. The compositions, expressed in g/kg of the aqueous and organic fractions separated, of the evaporate and of the evaporation residue, are given in Table 1 (M.C.=main constituent).

TABLE 1

| Constituent | Organic fraction separated | Aqueous fraction separated | Evaporation residue of the aqueous fraction | Evaporate |
|---|---|---|---|---|
| Water | 13 | M.C. | M.C. | M.C. |
| NaCl | 0.041 | 226.5 | 265 | |
| NaOH | | 0.16 | | |
| Epichlorohydrin | 891 | 11.1 | 0.09 | 79.0 |
| 1,3-Dichloro-2-propanol | 95 | 2.5 | <0.5 | 10.9 |
| 3-Chloro-1,2-propanediol | 0.2 | 0.44 | 0.7 | 14.2 |
| Glycerol | <0.1 | | <0.1 | |
| Chloroacetone | <0.1 | — | <0.1 | |
| Hydroxyacetone | <0.1 | <0.01 | <0.1 | |
| Glycidol | <0.1 | 2.6 | 0.07 | 0.13 |
| TOC (g C/l) | | 8.7 | 0.69 | |

EXAMPLE 2

A volume of aqueous composition containing 25% of NaCl and 2.6% of 3-chloro-1,2-propanediol was brought into contact with a half-volume of extraction solvent. After stirring vigorously for 30 minutes, the mixture was separated in a separating funnel. The 3-chloro-1,2-propanediol content was measured in each of the phases by chromatographic analysis and a partition coefficient of the 3-chloro-1,2-propanediol, corresponding to the ratio of the weight concentration of the 3-chloro-1,2-propanediol in the organic phase in g/kg to the weight concentration of the 3-chloro-1,2-propanediol in the aqueous phase in g/kg, was calculated. Table 2 repeats, for the exemplary solvents, the test temperature and also the concentrations obtained in each of the balanced phases and the calculated partition coefficients. LUBRIROB 926.65 is methyl oleate sold by Novance.

TABLE 2

| Solvent | Temperature (° C.) | 3-chloro-1,2-propanediol concentration in the extracted brine (g/kg) | 3-chloro-1,2-propanediol concentration in the organic extract (g/kg) | Partition coefficient (g/kg)/(g/kg) |
|---|---|---|---|---|
| 1-Octanol | 25 | 20 | 17 | 0.85 |
| 1-Decanol | 25 | 21 | 13 | 0.62 |
| 1-Dodecanol | 45 | 17 | 10 | 0.59 |
| 1-Tetradecanol | 60 | 22 | 8.8 | 0.40 |
| 1,2-Dodecanediol | 100 | 17 | 23 | 1.35 |
| 1,3-Dichloro-2-propanol (1,3-D) | 25 | 13 | 23 | 1.77 |
| 2,3-Dichloro-1-propanol (2,3-D) | 25 | 13 | 22 | 1.69 |
| 1,3-D/2,3-D 50/50 mixture g/g | 25 | 13 | 22 | 1.69 |
| LUBRIROB 926.65 | 25 | 25 | 0.93 | 0.04 |
| Di-n-butyl phthalate | 25 | 24 | 2.6 | 0.11 |
| Caprylic acid | 25 | 24 | 5 | 0.21 |
| Tri-n-octylphosphine oxide | 65 | 2.8 | 54 | 19.3 |

EXAMPLE 3

An aqueous composition was obtained containing 22.2% of NaCl, a TOC of 9.46 g C/kg, 38 g/kg of 1,3-dichloro-2-propanol and 0.59 g/kg of 2,3-dichloro-1-propanol and 0.07 g/kg of epichlorohydrin at the end of an extraction, via 1,3-dichloropropan-2-ol, of a second separated fraction, itself obtained at the end of a reaction between a mixture of dichloropropanol containing 1,3-dichloro-2-propanol and 2,3-dichloro-1-propanol, in which the 1,3-dichloro-2-propanol content, relative to the sum of the 1,3-dichloro-2-propanol and 2,3-dichloro-1-propanol contents, was at least 10% by weight, and a basic compound.

463.2 g of this aqueous composition were treated by a flow rate of 205 g/h of steam at a temperature of 85° C. under a pressure of 470 mbar.

A residual TOC in the aqueous composition of 1.65 g C/l, 0.35 g C/l, 0.10 g C/l and 0.06 g C/l was obtained after the passage of an accumulated amount of steam, which was 78 g, 157 g, 246 g and 335 g respectively.

EXAMPLE 4

One part of adsorbent was added to ten parts of an aqueous composition containing 20% of NaCl and 5 g/kg of 3-chloro-1,2-propanediol. The suspension was stirred at ambient temperature and aliquots were removed after 1 and 22 h. The amount of 3-chloro-1,2-propanediol was measured in the liquid recovered after filtration. Table 3 gives the results obtained.

TABLE 3

| Adsorbent | | 3-chloro-1,2-propanediol concentration in the treated aqueous composition after a contact time of 1 h (g/kg) | 3-chloro-1,2-propanediol concentration in the treated aqueous composition after a contact time of 22 h (g/kg) |
|---|---|---|---|
| PUROLITE resin | MN 270 | 1.32 | 1.36 |
| LEWATIT resin | UPOC 1163 | 0.85 | 1.00 |
| ALDRICH activated carbon | CAS 7440-44-O | 0.20 | 0.19 |
| BAKER activated carbon | Reference 1991 | 0.14 | 0.12 |
| CHEMVIRON activated carbon | CPG FE90219 F | 0.26 | 0.15 |
| CHEMVIRON activated carbon | CPG FE02416 A | 0.25 | 0.14 |
| CHEMVIRON activated carbon | C 1340 | 0.09 | 0.07 |

EXAMPLE 5

An oxidative treatment operation of an aqueous composition was carried out in a polytetrafluoroethylene-coated jacketed reactor, equipped with a magnetic stirrer bar and a draining system enabling a constant volume of 562 ml of liquid to be kept in the reactor. The treated aqueous composition was obtained from a separated fraction such as described in Example 3 previously extracted with 1,3-dichloro-2-propanol and steam-stripped and having a TOC of 505 mg C/l and was composed of 20% of NaCl and 1.4 g/kg of 1,3-dichloro-2-propanol. The oxidizing agent used was a sodium hypochlorite solution containing 11.2% g/g of NaOCl, 8.8% of NaCl and 2.0% of NaOH. The aqueous composition and the hypochlorite solution were introduced into the reactor at a constant flow rate of 1448 g/h and 109.2 g/h respectively. The reaction was carried out at 120° C. under an autogenous pressure of 4 bar. The aqueous composition recovered on exiting the reactor after cooling had a pH of 11.71 and a TOC of 230 mg C/l.

After 2 h of complementary treatment in a batch reactor at 120° C. under 4 bar absolute, the pH of the aqueous composition was 9.22 and the TOC measured was 13 mg of C/l. The composition of the aqueous compositions obtained is given in Table 4.

TABLE 4

| | | Aqueous composition after treatment in continuous reactor | Aqueous composition after treatment in batch reactor |
|---|---|---|---|
| pH | | 11.7 | 9.22 |
| TOC | (mg C/l) | 230 | 13 |
| NaOCl | (g/kg) | 6.1 | 0.5 |
| NaClO$_3$ | (g/kg) | 0.2 | 0.4 |
| NaCl | (g/kg) | 198 | 200 |
| Glycerol | (mg/l) | 140 | 0.01 |
| 1,3-Dichloro-2-propanol | (mg/l) | 0 | 0 |
| Propionic acid | (mg/l) | 30 | 0.5 |
| Formic acid | (mg/l) | 322 | 3.5 |
| Acetic acid | (mg/l) | 0.5 | 3 |
| Glycolic acid | (mg/l) | 204 | 4.5 |
| Lactic acid | (mg/l) | 0.5 | 0.5 |
| Formaldehyde | (mg/l) | 0.06 | 0.03 |
| Glyceraldehyde | (mg/l) | 0.2 | 0 |
| Acetaldehyde | (mg/l) | 0.005 | 0.005 |
| Hydroxyacetone | (mg/l) | 0.4 | 0.5 |
| Acetone | (mg/l) | 0.005 | 0.005 |

EXAMPLE 6

An oxidative treatment operation of an aqueous composition has been carried out continuously in a cascade of 3 thermostatised glass reactors; the two first reactors were stirred with a magnetic stirring bar and the last reactor was of the plug flow type. The treated aqueous composition was obtained from a separated fraction such as described in Example 3. The aqueous composition has a TOC value of 1.4 gC/l and a Chemical Oxygen Demand (COD) value of 3.9 g O/l. Its composition is given in Table 5. The aqueous composition has been continuously fed in the first reactor. The oxidizing agent used was a sodium hypochlorite solution containing 10.2% g/g of NaOCl, 8.2% of NaCl and 2.3% of NaOH. A part of the hypochlorite solution (1.2 equivalent to the COD of the effluent) has continuously been introduced into the first reactor and a second part of hypochlorite (0.8 equivalent to the COD of the effluent) has continuously been added to the second reactor at constant flow rates. The pH has been regulated at 8.5 (measured at 25° C. after sampling) in the two stirred reactors by addition of concentrated hydrochloric acid. The temperature has been maintained at 105° C., the pressure has been maintained at 1 bar absolute and the residence time has respectively been of 66, 56 et and 47 min in the first, the second and the third reactor. The aqueous composition which has been recovered on exiting the third reactor after cooling had a pH of 7.4 and a TOC of 60 mg C/l. The composition of the aqueous composition obtained after treatment is given in Table 5.

TABLE 5

| | | Aqueous composition before oxidation treatment | Aqueous composition after oxidation treatment |
|---|---|---|---|
| pH at 25° C. | | 9.3 | 7.4 |
| TOC | (mg C/l) | 1400 | 59 |
| NaOCl | (g/kg) | | 1.0 |
| NaClO$_3$ | (g/kg) | | 6.2 |
| NaCl | (g/kg) | 160 | 154 |
| Glycidol | (g/kg) | 0.39 | 0 |
| Glycerol | (g/kg) | 0.69 | 0 |
| 3-chloro-1,2-propanediol | (g/kg) | 0.59 | 0 |
| 2-chloro-1,3-propanediol | (g/kg) | 0.08 | 0 |
| 1,3-Dichloro-2-propanol | (mg/l) | 0 | 0 |
| Propionic acid | (mg/l) | 12 | 8 |
| Formic acid | (mg/l) | 50 | 4 |
| Acetic acid | (mg/l) | 73 | 110 |
| Glycolic acid | (mg/l) | <1 | <1 |
| Lactic acid | (mg/l) | 18 | <1 |
| Formaldehyde | (mg/l) | 0.8 | 0.3 |
| Glyceraldehyde | (mg/l) | 1 | 0.04 |
| Acetaldehyde | (mg/l) | 0.5 | 0.03 |
| Hydroxyacetone | (mg/l) | 80 | 1.2 |
| Acrolein | (mg/l) | 0.2 | 0.03 |
| Acetone | (mg/l) | 0.06 | <0.01 |

EXAMPLE 7

A composition classically used as starting material in a membrane electrolysis process has been obtained. That composition comprised 250 g of NaCl per kg and had a TOC content of 3 mg C/l.

An electrolysis cell of 0.6 liter, comprising an anolyte chamber with one anode and a catholyte chamber with one cathode, separated by a membrane, has been used. The anode consisted of a Titanium substrate on which an electrochemical coating has been applied. The cathode consisted of a nickel substrate on which an electrochemical coating has been applied. The membrane was an Asahi Glas Company—Flemion F8020 membrane. The catholyte chamber has been continuously fed with an aqueous composition containing 29% by weight of NaOH at a rate of 0.4 l/h. The anolyte chamber has been fed with the above mentioned aqueous composition. The residence time of the aqueous composition in the anolyte chamber was 53 min. A direct current density of 4 kA per m$^2$ of electrode has been applied between the anode and the cathode. The temperature of cell has been maintained at 85° C. and the pressure at 1 bar absolute. The difference of voltage between the anode and the cathode has been recorded with time on stream. The current yield has been calculated according to a formula based on the presence of secondary components present in the anolyte and chlorine well known by those skilled in the art of chlor-alkali electrolysis.

The cell has been operated under such conditions for 125 days. The cell voltage stabilized between 3.0 and 3.1 V. The current yield stabilized between 98 and 98.7%.

After 125 days, acetic acid has been added to the aqueous composition feeding the anolyte chamber so as to obtain a concentration of 5 g/l (TOC of 2 g CA). The cell voltage remained unchanged and the current yield increased initially to 99.0-99.5%. The current yield remained higher than its value before adding acetic acid for 120 days with time on stream.

No foaming has been observed neither in the anolyte nor in the catholyte chamber at any time.

The invention claimed is:

1. An aqueous composition comprising at least one salt in an amount of at least 50 g/kg of composition and at least one carboxylic acid, said composition having a total organic carbon content of at least 1 µg of C/l and at most 2 g of C/l of composition.

2. The aqueous composition according to claim 1, wherein the carboxylic acid comprises from 1 to 10 carbon atoms.

3. The aqueous composition according to claim 1, comprising polyvalent metals in a content which is less than or equal to 0.5 mg of polyvalent metals per kg of aqueous composition.

4. The aqueous composition according to claim 1, containing active chlorine in a content greater than or equal to 0.001 mg Cl$_2$ per kg of aqueous composition and lower than or equal to 1 g Cl$_2$ per kg of aqueous composition.

5. The aqueous composition according to claim 1, containing an additional organic compound selected from the group consisting of acetone, acrolein, 2-butanone, isopropanol, 3-methoxy-1,2-epoxypropane, cyclopentanone, epichlorohydrin, chloroacetone, hydroxyacetone (acetol), C$_6$H$_{12}$O, 1,2,3-trichloropropane, 2,3-epoxy-1-propanol (glycidol), 2-chloro-2-propen-1-ol, 3-chloro-2-propen-1-ol cis, 1-methoxy-3-chloropropane-2-ol, 3-chloro-1-propane-1-ol, 3-chloro-2-propen-1-ol trans, C$_6$H$_8$O$_2$, C$_6$H$_{12}$OCl$_2$, C$_6$H$_{10}$O$_2$Cl$_2$, 1,3-dichloro-2-propanol, C$_9$H$_{10}$O$_2$, 2,3-dichloro-1-propanol, phenol, glycerol, 1-chloro-2,3-propanediol, 2-chloro-1,3-propanediol, glycerol, cyclic diglycerols, glyceraldehydes, formaldehyde, acetaldehyde, propionaldehyde, butyraldehyde, and mixtures thereof.

6. A process for manufacturing the aqueous composition according to claim 1, comprising:
   a) in a liquid reaction medium, a mixture of dichloropropanol comprising 1,3-dichloro-2-propanol and 2,3-dichloro-1-propanol, in which the 1,3-dichloro-2-propanol content, relative to the sum of the 1,3-dichloro-2-propanol and 2,3-dichloro-1-propanol contents, is at least 10% by weight, is reacted with at least one basic compound in order to form epichlorohydrin and at least one salt;

b) at least one part of the liquid reaction medium from a) is subjected to a settling operation in which a first fraction comprising most of the epichlorohydrin which was comprised in the part of the reaction medium from a) before the settling operation is separated from a second fraction comprising most of the salt which was comprised in the part of the reaction medium from a) before the settling operation; and c) the second fraction separated in b) is subjected to at least one treatment selected from the group consisting of a physical treatment, a chemical treatment, a biological treatment, and any combination thereof to produce the aqueous composition according to claim 1.

7. The process according to claim 6, wherein the physical treatment is selected from the group consisting of dilution, concentration, evaporation, distillation, stripping, liquid/liquid extraction, and adsorption operations, alone or in combination, the chemical treatment is selected from the group consisting of oxidation, reduction, neutralization, complexation, and precipitation operations, alone or in combination, and the biological treatment is selected from the group consisting of an aerobic bacterial treatment and an anaerobic bacterial treatment, alone or in combination.

8. The process according to claim 6, wherein the treatment comprises at least one stripping operation carried out with steam followed by at least one oxidation operation carried out in the presence of an oxidizing agent containing active chlorine.

9. The process according to claim 8, wherein the treatment comprises in addition at least one liquid/liquid extraction operation with a mixture of 1,3-dichloro-2-propanol and 2,3-dichloro-1-propanol wherein the liquid/liquid extraction is carried out before the stripping operation.

10. The process according to claim 6, wherein a) to c) are carried out in equipment produced from or covered with materials that are resistant to the basic compound under the a) reaction conditions, b) settling conditions and c) treatment conditions, and resistant to the oxidizing agent under the c) treatment conditions, the materials that are resistant to the basic compound being selected from the group consisting of carbon steel, stainless steel, nickel, enamelled steel, polypropylene, and polytetrafluoroethylen; and the materials that are resistant to the oxidizing agent being selected from the group consisting of titanium, enamelled steel, and Hastelloy C.

11. The aqueous composition according to claim 1, wherein the salt is sodium chloride.

12. The aqueous composition according to claim 11, wherein the salt is present in an amount of at least 160 g/kg, the total organic carbon content is at most 0.01 g C/l, and wherein the aqueous composition comprises acetic acid.

13. The aqueous composition according to claim 1, wherein the salt is present in an amount of at least 160 g/kg.

14. The aqueous composition according to claim 1, wherein the salt is present in an amount of at least 200 g/kg.

15. The aqueous composition according to claim 1, wherein the total organic carbon content is at most 1 g C/l.

16. The aqueous composition according to claim 1, wherein the total organic carbon content is at most 0.1 g C/l.

17. The aqueous composition according to claim 1, wherein the total organic carbon content is at most 0.01 g C/l.

18. The aqueous composition according to claim 1, comprising at least one carboxylic acid selected from the group consisting of formic acid, acetic acid, propionic acid, glycolic acid, and lactic acid.

19. The aqueous composition according to claim 1, comprising acetic acid.

* * * * *